(12) United States Patent
Xiao et al.

(10) Patent No.: US 8,771,807 B2
(45) Date of Patent: Jul. 8, 2014

(54) ORGANOAMINOSILANE PRECURSORS AND METHODS FOR MAKING AND USING SAME

(75) Inventors: Manchao Xiao, San Diego, CA (US);
Xinjian Lei, Vista, CA (US); Bing Han, Beijing (CN); Mark Leonard O'Neill, San Marcos, CA (US); Ronald Martin Pearlstein, San Marcos, CA (US); Richard Ho, Anaheim, CA (US); Haripin Chandra, Carlsbad, CA (US); Agnes Derecskei-Kovacs, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 13/474,076

(22) Filed: May 17, 2012

(65) Prior Publication Data

US 2013/0129940 A1 May 23, 2013

Related U.S. Application Data

(60) Provisional application No. 61/489,486, filed on May 24, 2011.

(51) Int. Cl.
*C07F 7/02* (2006.01)
(52) U.S. Cl.
USPC .......... 427/578; 556/410; 556/412; 546/14; 544/69; 544/227; 548/406
(58) Field of Classification Search
None
See application file for complete search history.

(56) References Cited

U.S. PATENT DOCUMENTS

| 4,200,666 A | 4/1980 | Reinberg |
| 4,863,755 A | 9/1989 | Hess et al. |
| 4,992,299 A | 2/1991 | Hochberg et al. |
| 5,008,422 A | 4/1991 | Blum et al. |
| 5,234,869 A | 8/1993 | Mikata et al. |
| 5,250,473 A | 10/1993 | Smits |
| 5,382,550 A | 1/1995 | Iyer |
| 5,458,689 A | 10/1995 | Saito |

(Continued)

FOREIGN PATENT DOCUMENTS

| EP | 0 481 706 A1 | 4/1992 |
| EP | 1149934 | 8/2005 |

(Continued)

OTHER PUBLICATIONS

E.W. Abel The Reactions of Hexamethyldisilthiane and Ethylthiotrimethylsilane with Alcohols, Thiols, Acids, and Amines, J. Chem. Soc. 1961, 4933-4935.*

(Continued)

*Primary Examiner* — Robert S Loewe
(74) *Attorney, Agent, or Firm* — Rosaleen P. Morris-Oskanian

(57) ABSTRACT

Described herein are organoaminosilane precursors which can be used to deposit silicon containing films which contain silicon and methods for making these precursors. Also disclosed herein are deposition methods for making silicon-containing films or silicon containing films using the organoaminosilane precursors described herein. Also disclosed herein are the vessels that comprise the organoaminosilane precursors or a composition thereof that can be used, for example, to deliver the precursor to a reactor in order to deposit a silicon-containing film.

10 Claims, 7 Drawing Sheets

(56) References Cited

U.S. PATENT DOCUMENTS

| | | |
|---|---|---|
| 5,622,784 A | 4/1997 | Okaue et al. |
| 5,656,076 A | 8/1997 | Kikkawa |
| 5,772,757 A | 6/1998 | Saito |
| 5,837,056 A | 11/1998 | Kikkawa |
| 5,874,368 A | 2/1999 | Laxman et al. |
| 6,153,261 A | 11/2000 | Xia et al. |
| 6,268,299 B1 | 7/2001 | Jammy et al. |
| 6,391,803 B1 | 5/2002 | Kim et al. |
| 6,486,015 B1 | 11/2002 | Chaudhary et al. |
| 6,486,083 B1 | 11/2002 | Mizuno et al. |
| 6,500,772 B2 | 12/2002 | Chakravarti et al. |
| 6,559,074 B1 | 5/2003 | Chen et al. |
| 6,586,056 B2 | 7/2003 | Arkles et al. |
| 6,630,413 B2 | 10/2003 | Todd |
| 6,716,772 B2 | 4/2004 | Mizuno et al. |
| 6,890,869 B2 | 5/2005 | Chung |
| 6,974,780 B2 | 12/2005 | Schuegraf |
| 7,098,150 B2 | 8/2006 | Misra et al. |
| 7,122,222 B2 | 10/2006 | Xiao et al. |
| 7,125,582 B2 | 10/2006 | McSwiney et al. |
| 7,172,792 B2 | 2/2007 | Wang et al. |
| 7,332,618 B2 | 2/2008 | Meiere |
| 7,351,670 B2 | 4/2008 | Hoshi et al. |
| 7,365,029 B2 | 4/2008 | Iyer et al. |
| 7,446,217 B2 | 11/2008 | Wang et al. |
| 7,462,376 B2 | 12/2008 | Kato et al. |
| 7,473,655 B2 | 1/2009 | Wang et al. |
| 7,482,286 B2 | 1/2009 | Misra et al. |
| 7,510,984 B2 | 3/2009 | Saito et al. |
| 7,531,679 B2 | 5/2009 | Wang et al. |
| 7,601,652 B2 | 10/2009 | Singh et al. |
| 7,651,961 B2 | 1/2010 | Clark |
| 7,713,346 B2 | 5/2010 | Wang et al. |
| 7,786,320 B2 | 8/2010 | Wang et al. |
| 7,875,556 B2 | 1/2011 | Xiao et al. |
| 7,932,413 B2 | 4/2011 | Xiao et al. |
| 2002/0086541 A1 | 7/2002 | Fu et al. |
| 2002/0175393 A1 | 11/2002 | Baum et al. |
| 2003/0124818 A1 | 7/2003 | Luo et al. |
| 2005/0048204 A1 | 3/2005 | Dussarrat et al. |
| 2005/0085098 A1 | 4/2005 | Timmermans et al. |
| 2005/0163927 A1 | 7/2005 | McSwiney et al. |
| 2006/0022803 A1 | 2/2006 | Akiyama et al. |
| 2006/0045986 A1 | 3/2006 | Hochberg et al. |
| 2006/0051975 A1 | 3/2006 | Misra et al. |
| 2006/0062913 A1 | 3/2006 | Wang et al. |
| 2006/0099831 A1 | 5/2006 | Borovik et al. |
| 2006/0216950 A1 | 9/2006 | Matsuura |
| 2006/0228903 A1 | 10/2006 | McSwiney et al. |
| 2006/0258173 A1 | 11/2006 | Xiao et al. |
| 2007/0160774 A1 | 7/2007 | Tsukada et al. |
| 2007/0275166 A1 | 11/2007 | Thridandam et al. |
| 2008/0038936 A1 | 2/2008 | Todd et al. |
| 2008/0260969 A1 | 10/2008 | Dussarrat et al. |
| 2009/0069588 A1 | 3/2009 | Xiao et al. |
| 2009/0075490 A1 | 3/2009 | Dussarrat |
| 2009/0205568 A1 | 8/2009 | Mizuno et al. |
| 2010/0209624 A1 | 8/2010 | Matsuura |
| 2011/0136347 A1* | 6/2011 | Kovarsky et al. ............ 438/758 |
| 2011/0178322 A1* | 7/2011 | Hamada et al. ............ 556/412 |
| 2012/0178953 A1 | 7/2012 | Ma et al. |
| 2013/0022745 A1 | 1/2013 | Dussarrat et al. |

FOREIGN PATENT DOCUMENTS

| | | |
|---|---|---|
| EP | 1724373 A1 | 11/2006 |
| EP | 1967609 | 9/2008 |
| EP | 2392691 | 6/2011 |
| GB | 1123252 | 8/1968 |
| JP | 6132276 | 5/1994 |
| JP | 06132284 | 5/1994 |
| JP | 07235535 | 9/1995 |
| JP | 8227890 | 9/1996 |
| JP | 00195801 | 7/2000 |
| JP | 2001156063 | 6/2001 |
| JP | 200526244 | 1/2005 |
| JP | 2009516906 A | 4/2009 |
| JP | 2010043081 | 2/2010 |
| JP | 2012532193 A | 12/2012 |
| KR | 1020050018641 | 2/2006 |
| WO | 02065508 | 8/2002 |
| WO | 2004010467 | 1/2004 |
| WO | 2004017383 | 2/2004 |
| WO | 2004030071 | 4/2004 |
| WO | 2005080628 | 9/2005 |
| WO | 2005093126 | 10/2005 |
| WO | 2006036538 | 4/2006 |
| WO | 2006097525 | 9/2006 |
| WO | 2007002040 A2 | 1/2007 |
| WO | 2011005653 A1 | 1/2011 |

OTHER PUBLICATIONS

Anderson et al. Isopropyldisilylamine and Disilyl-t-butylamine: Preparation, Spectroscopic Properties, and Molecular Structure in the Gas Phase, determined by Electron Diffraction, J. Chem. Soc. Dalton Trans. 1989, 779-783.*

Norman et al. "Reaction of Silylphosphine with Ammonia" Inorganic Chemistry, 18(6), 1979, 1594-1597.*

Drake et al. "Chlorosilylamines" J. Chem. Soc. (A), 1971, 3617-3620.*

R.G. Gordon, et al, Silicon Dimethylamido Complexes and Ammonia as Precursors for the Atmospheric Pressure Chemical Vapor Deposition of Silicon Nitride Thin Films, American Chemical Society, 1990, 480-482.

D.M, Hoffman, et al, Plasma enhanced chemical vapor deposition of silicon nitride films from a metal-organic precursor, Materials Research Society, 1994, 3019-3021.

A. Kikkawa, et al, Electrical properties of silicon nitride films deposited by catalytic chemical vapor deposition on catalytically nitrided Si(100), Thin Solid Films, 2003, 100-103.

S. Yokoyama, et al, Atomic-layer selective deposition of silicon nitride on hydrogen-terminated Si surfaces, Applied Surface Science, 1998, 352-356.

Nekrasov, Y.S., et al, On the Relationship between the Mass Spectral and Structural Indices of Arylsilanes, Russian Chemical Bulletin, vol. 42, No. 2, Feb. 1993, 343-346.

Egorochkin, A.N., et al, d(pi)-p(pi) Interaction in Bonds of Silicon with Nitrogen and Phosphorus, Bulletin of the Academy of Sciences of the Ussr, Div. of Chemical Sciences, vol. 19, No. 11, Nov. 1970, 2454-2456.

Aylett, B.J., et al, Silicon Nitrogen Compounds. Part VII. N-Silyl Derivatives of Analine, Journals of the Chemicals Society. A, Inorganice, Physical and Theoretical CHemistry, 1969, 800-803.

Aylett, B.J., et al, Silicon Nitrogen Compounds. Part VI. The Preparation and Properties of Disilazane, Journals of the Chemical Society. A, Inorganic, Physical and Theoretical Chemistry, 1969, 639-642.

Gary E. McGuire, Semiconductor Materials and Process Technology Handbook, Noyes Publications, NJ, 1988, pp. 239-301.

Stanley Wolf, Silicon Processing for the VLSI Era, Lattice Press, CA 1990, pp. 327-330.

Arthur K. Hochberg, et al, Diethylsilane as a Source for the Deposition . . . , Mat. Res. Soc, Symp. Proc., vol. 204, 1991, pp. 509-513.

Tetsuji Sorita, et al, Mass Spectrometric and Kinetic Study of Low-Pressure . . . , J. Elec. Soc., vol. 141, No. 12, 1994, pp. 3506-3511.

B.J. Aylett, et al, The Preparation and Properties of Dimethylamino- and . . . , J. Chem. Soc. (A), 1967, pp. 652-655.

Sei Sujishi, et al, Effect of Replacement of Carbon by Silicon in Trimethylamine . . . , J. Am. Chem. Soc., vol. 78, 1956, pp. 4631-4636.

Kenneth Hedberg, The Molecular Structure of Trisilylamine (SiH3) 3N1, 2, J. Am. Chem. Soc., 1955, vol. 77, pp. 6491-6492.

J.M. Grow, et al, Growth Kinetics and Characterization of Low Pressure . . . , Mat. Letters vol. 23, 1995, pp. 187-193.

B.A. Scott, et al, Preparation of Silicon Nitride with Good Interface . . . , Chemtronics, 1989, vol. 4, pp. 230-233.

B.J. Aylett, et al, Silicon-Nitrogen Compounds. Part V. Diphenylamino-derivatives of Silane, J. Chem. Soc., 1989, 636-639.

(56) References Cited

OTHER PUBLICATIONS

Norbert W. Mizel, Simple Silylhydrazines as Models for Si—N beta.-donor Interactions in SiNN Units, Chemistry—A European Journal, 1998, 692-698.

Hubert Schmidbuar, et al, Differences in Reactivity of 1,4-Disilabutane and N-Tetrasilane Towards Secondary Amines, Zeitschrift Fur Naturforschung B: Chemical Sciences, 1990, 1679-1683.

A.V. Golubinszkij, et al, Molecular-structure Examination of Some Organic Silicon Compounds by Electron Diffraction, Kemiai Kozlemenyek, 46, 1976, 473-480.

C. Glidewell, et al, Electron Diffraction Determination of the Molecular Structure of Tetrasilylhydrazine, Journal of the Chemical Society, 1970, 318-320.

H. Beck, et al, Radical Ions. 36. Structural Changes Accompanying the One-Electron Oxidation of Hydrazine and Its Silyl Derivatives1-3, Journal of the American Chemical Society, 1980, 4421-4428.

B.J. Aylett, The Silyl Group as an Electron Acceptor, J. Inorg. Nucl. Chem., 1956, 325-329.

N. Bingo, et al, Correlations Among X—H Bond Lengths, X—H Stretching Frequencies, and Bond Order Matrix Elements P HX: where X=C, N, and Si, J. Sci. Hiroshima Univ., 1976, 317-326.

B.J. Aylett, Vibrational spectra and structure of tetrasilylhydrazine and tetrasilylhydrazine-d, Spectrochimica Acta, 1960, 747-758.

C. Glidewell, et al, Some Preparative and Spectroscopic Studies of Silylamines, Journal of the Chemical Society A Inorg. Phys. Theor, 1970, 279-286.

B.J. Aylett, et al, N-Silyl Derivatives of Cyclic Secondary Amines, J. Chem. Soc, 1967, 1918-1921.

B.J. Aylett, et al, Silicon-Nitrogen Compounds. Part VIII. Base-Promoted Disproportionation of N-Methly- and N-Phenyl-Disilazane, J. Chem. Soc., 1969, 1788-1792.

D. Anderson, et al, Isopropyldisilylamine and Disilyl-t-butylamine: Preparation, Spectroscopic Properties, and Molecular Structure in the Gas Phase, determined by Electron Diffraction, J. Chem. Soc., 1989, 779-783.

\* cited by examiner

ORGANOAMINOSILANE PRECURSORS AND METHODS FOR MAKING AND USING SAME

CROSS-REFERENCE TO RELATED APPLICATIONS

This application claims the priority benefit under 35 U.S.C. §119 of the following application: U.S. Provisional Application No. 61/489,486 filed 24 May 2011, the disclosure of which is incorporated herein by reference in its entirety.

BACKGROUND OF THE INVENTION

Precursors, particularly organoaminosilane precursors that can be used for the deposition of silicon containing films, including but not limited to, silicon containing films such as amorphous silicon, crystalline silicon, silicon nitride, silicon oxide, silicon carbonitride, and silicon oxynitride films are described herein. In yet another aspect, described herein is the use of the organoaminosilane precursors for depositing silicon-containing silicon containing films in the fabrication of integrated circuit devices. In these or other aspects, the organoaminosilane precursors may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LPCVD"), and atmospheric pressure chemical vapor deposition.

Several classes of compounds can be used as precursors for silicon-containing films such as, but not limited to, silicon oxide or silicon nitride films. Examples of these compounds suitable for use as precursors include silanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

Low pressure chemical vapor deposition (LPCVD) processes are one of the more widely accepted methods used by semiconductor industry for the deposition of silicon-containing films. Low pressure chemical vapor deposition (LPCVD) using ammonia may require deposition temperatures of greater than 750° C. to obtain reasonable growth rates and uniformities. Higher deposition temperatures are typically employed to provide improved film properties. One of the more common industry methods to grow silicon nitride or other silicon-containing films is through low pressure chemical vapor deposition in a hot wall reactor at temperatures >750° C. using the precursors silane, dichlorosilane, and/or ammonia. However, there are several drawbacks using this method. For example, certain precursors, such as silane, are pyrophoric. This may present problems in handling and usage. Also, films deposited from silane and dichlorosilane may contain certain impurities. For example, films deposited using dichlorosilane may contain certain impurities, such as chlorine and ammonium chloride, which are formed as byproducts during the deposition process. Films deposited using silane may contain hydrogen.

Japanese Publ. No. 6-132284 describes a method for forming by chemical vapor deposition a silicon nitride film using as a starting gas which is "an organosilane compound represented by the general formula $(R^1R^2N)_nSiH_{4-n}$ (where groups $R^1$ and $R^2$ are any of H—, $CH_3$—, $C_2H_5$—, $C_3H_7$—, and $C_4H_9$—, at least one of which not being H—, and n is an integer of 1 through 4). Claim 3 recites that the "organosilane compound is trisdimethylaminosilane $((CH_3)_2N)_3SiH$, bisdimethylaminosilane $((CH_3)_2N)_2SiH_2$, dimethylaminosilane $((CH_3)_2N)SiH_3$, trisdiethylaminosilane $((C_2H_5)_2N)_3SiH$, bisdiethylaminosilane $((C_2H_5)_2N)_2SiH_2$, diethylaminosilane $((C_2H_5)_2N)SiH_3$, trisdipropylaminosilane $((C_3H_7)_2N)_3SiH$, bisdipropylaminosilane $((C_3H_7)_2N)_2SiH_2$, dipropylaminosilane $((C_3H_7)_2N)SiH_3$, trisdiisobutylaminosilane $((C_4H_9)_2N)_3SiH$, bisdiisobutylaminosilane $((C_4H_9)_2N)_2SiH_2$, and diisobutylaminosilane $((C_4H_9)_2N)SiH_3$.

U.S. Pat. No. 6,391,803 describes an atomic layer deposition method of forming a thin film layer containing silicon such as $Si_3N_4$ and $SiO_2$ thin films using a first reactant which is preferably $Si[N(CH_3)_2]_4$, $SiH[N(CH_3)_2]_3$, $SiH_2[N(CH_3)_2]_2$ or $SiH_3[N(CH_3)_2]$ and a second reactant which is preferably activated $NH_3$.

Japanese Publ. No. 6-132276 describes method of forming silicon oxide film by CVD using oxygen and organic silane compound represented by general formula $(R^1R^2N)_nSiH_{4-n}$ (where $R^1$ and $R^2$ are H—, $CH_3$—, $C_2H_5$—, $C_3H_7$—, and $C_4H_9$—, at least one of which not H—, and n is an integer of 1 through 4). Claim 3 recites that the "organic silane compound is trisdimethylaminosilane $((CH_3)_2N)_3SiH$, bisdimethylaminosilane $((CH_3)_2N)_2SiH_2$, dimethylaminosilane $((CH_3)_2N)_3SiH$, trisdiethylaminosilane $((C_2H_5)_2N)_3SiH$, bisdiethylaminosilane $((C_2H_5)_2N)_2SiH_2$, diethylaminosilane $((C_2H_5)_2N)SiH_3$, trisdipropylaminosilane $((C_3H_7)_2N)_3SiH$, bisdipropylaminosilane $((C_3H_7)_2N)_2SiH_2$, dipropylaminosilane $((C_3H_7)_2N)SiH_3$, trisdiisobutylaminosilane $((C_4H_9)_2N)_3SiH$, bisdiisobutylaminosilane $((C_4H_9)_2N)_2SiH_2$, and diisobutylaminosilane $((C_4H_9)_2N)SiH_3$".

Applicants' patents, U.S. Pat. Nos. 7,875,556; 7,875,312; and 7,932,413, described classes of aminosilanes which are used for the deposition of dielectric films, such as, for example, silicon oxide and silicon carbonitride films in a chemical vapor deposition or atomic layer deposition process.

Applicants' pending application, EP Publ. No. 2,392,691 which is related to U.S. application Ser. No. 13/114,287 describes precursors that are used for the deposition of silicon containing films.

Precursors that are used in depositing silicon nitride films such as BTBAS and chlorosilanes generally deposit the films at temperatures greater than 550° C. The trend of miniaturization of semiconductor devices and low thermal budget requires lower process temperatures and higher deposition rates. The temperature, at which the silicon containing films are deposited, should decrease in order to prevent ion diffusion in the lattice, particularly for those substrates comprising metallization layers and on many Group III-V and II-VI devices. Accordingly, there is a continuing need in the art to provide new and more cost effective precursors for the deposition of silicon-containing films, such as silicon oxide or silicon nitride films, that are sufficiently chemically reactive to allow deposition via CVD, ALD or other processes at temperatures of 550° C. or below or even at room temperature yet stable enough for normal processing and handling requirements.

BRIEF SUMMARY OF THE INVENTION

Described herein are organoaminosilane precursors and methods using same for forming films comprising silicon (referred to herein as silicon containing films), such as, but not limited to, amorphous silicon, crystalline silicon, semi-crystalline silicon, stoichiometric or non-stoichiometric silicon oxide, stoichiometric or non-stoichiometric silicon nitride, silicon oxynitride, silicon carbide, silicon carbonitride, and combinations thereof onto at least a portion of a substrate. Also disclosed herein are the methods to form silicon containing films or coatings on an object to be processed, such as, for example, a semiconductor wafer. In one embodiment of the method described herein, a layer comprising silicon and oxygen is deposited onto a substrate using an organoaminosilane precursor and an oxidizing agent in a deposition chamber under conditions for generating a silicon oxide layer on the substrate. In another embodiment of the method described herein, a layer comprising silicon and nitrogen is deposited onto a substrate using an organoaminosilane precursor and an nitrogen containing precursor in a deposition chamber under conditions for generating a silicon nitride layer on the substrate. In a further embodiment, the organoaminosilane precursors described herein can also be used a dopant for metal containing films, such as but not limited to, metal oxide films or metal nitride films.

In the processes described herein, at least one organoaminosilane having Formula A, B, and C or mixtures thereof is employed as at least one of the silicon containing precursors:

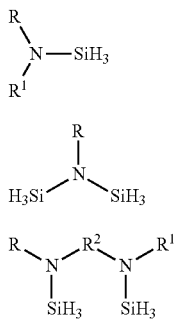

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group. In certain embodiments of Formula A, R and $R^1$ can be combined to form a cyclic or alkyl substituted cyclic group. In certain embodiments of Formula C, any one or more of R, $R^2$, and $R^1$ can be combined to form a cyclic group. In other embodiments of Formula A or C, R and $R^1$ or any one or R, $R^2$, and $R^1$, respectively, are not combined to form a cyclic group. In one particular embodiment, the organoaminosilane precursor has the Formula A wherein R is n-propyl and $R^1$ is isopropyl. In these or other embodiments of Formula A, R and $R^1$ are different substituents and the organoaminosilane is an asymmetrical molecule. In another embodiment of Formula A, R and $R^1$ are the same substituents and the organoaminosilane is a symmetrical molecule. In a preferred embodiment of Formula A, R is a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In one aspect, the organoaminosilane precursor described herein comprises at least one precursor having Formula A, B, and C is employed as at least one of the silicon containing precursors:

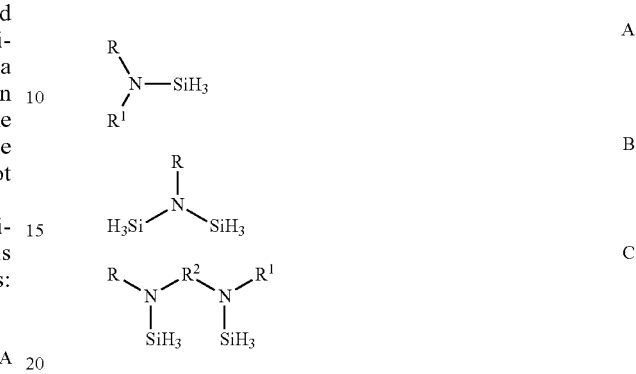

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group. In certain embodiments of Formula A, R and $R^1$ can be combined to form a cyclic or alkyl substituted cyclic group. In certain embodiments of Formula C, any one or more of R, $R^2$, and $R^1$ can be combined to form a cyclic group. In other embodiments of Formula A or C, R and $R^1$ or any one or R, $R^2$, and $R^1$, respectively, are not combined to form a cyclic group. In one particular embodiment, the organoaminosilane precursor has the formula A wherein R is n-propyl and $R^1$ is isopropyl. In these or other embodiments of Formula A, R and $R^1$ are different substituents and the organoaminosilane is an asymmetrical molecule. In another embodiment of Formula A, R and $R^1$ are the same substituents and the organoaminosilane is a symmetrical molecule.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process from an at least one organoaminosilane having Formula A, B, and C or mixtures thereof is employed as at least one of the silicon containing precursors:

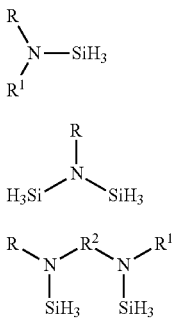

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group. In certain embodiments of Formula A, R and $R^1$ can be combined to form a cyclic or alkyl substituted cyclic group. In one particular embodiment, the organoaminosilane comprises a Formula A precursor wherein R is selected from a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In another aspect, there is provided a method of forming a silicon oxide film via an atomic layer deposition process, the method comprising the steps of:
  a. providing a substrate in a reactor;
  b. introducing into the reactor an at least one silicon precursor selected from an at least one organoaminosilane having Formula A, B, and C or mixtures thereof is employed as at least one of the silicon containing precursors:

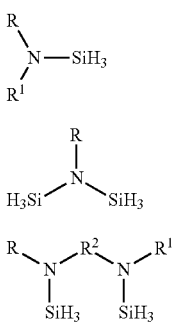

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group;
  c. purging the reactor with a purge gas;
  d. introducing an oxygen source into the reactor;
  e. purging the reactor with a purge gas; and
  f. repeating the steps b through e until a desired thickness of the film is obtained. In one particular embodiment of the method described herein, the organoaminosilane comprises a Formula A precursor wherein R is selected from a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In a further aspect, there is provided a method of forming a silicon oxide film onto at least a surface of a substrate using a CVD process comprising:
  a. providing a substrate in a reactor;
  b. introducing into the reactor at least one organoaminosilane having Formula A, B, and C or mixtures thereof:

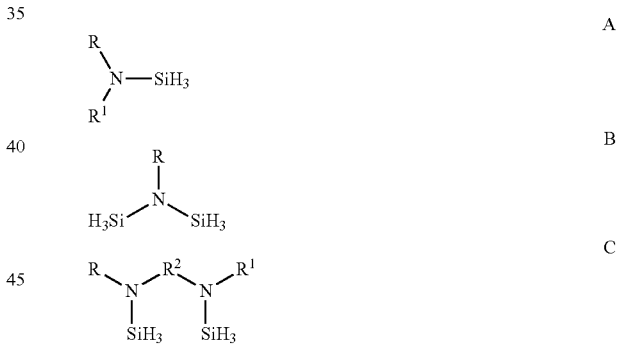

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group; and c. providing an oxygen source to deposit the silicon oxide film onto the at least one surface. In one particular embodiment of the method described herein, the organoaminosilane comprises a Formula A precursor wherein R is selected from a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In another aspect, there is provided a method of forming a silicon nitride film via an atomic layer deposition process, the method comprising the steps of:

a. providing a substrate in a reactor;
b. introducing into the reactor at least one organoaminosilane having Formula A, B, and C or mixtures thereof is employed as at least one of the silicon containing precursors:

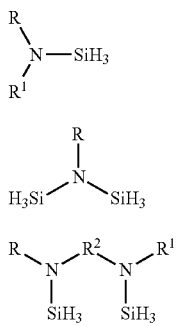

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_2$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group;

c. purging the reactor with a purge gas;
d. introducing a nitrogen-containing source into the reactor;
e. purging the reactor with a purge gas; and
f. repeating the steps b through e until a desired thickness of the silicon nitride film is obtained. In one particular embodiment of the method described herein, the organoaminosilane comprises a Formula A precursor wherein R is selected from a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In a further aspect, there is provided a method of forming a silicon nitride film onto at least a surface of a substrate using a CVD process comprising:

a. providing a substrate in a reactor;
b. introducing into the reactor at least one organoaminosilane having Formula A, B, and C or mixtures thereof is employed as at least one of the silicon containing precursors:

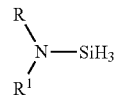

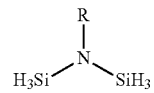

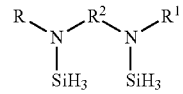

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group;

c. providing a nitrogen-containing source wherein the at least one organoaminosilane precursors and the nitrogen-containing source react to deposit the film comprising both silicon and nitrogen onto the at least one surface. In one particular embodiment of the method described herein, the organoaminosilane comprises a Formula A precursor wherein R is selected from a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In another aspect, a vessel for depositing a silicon containing film comprising one or more organoaminosilane precursor having Formula A, B, C, or mixtures thereof is described herein. In one particular embodiment, the vessel comprises at least one pressurizable vessel (preferably of stainless steel) fitted with the proper valves and fittings to allow the delivery of one or more precursors to the reactor for a CVD or an ALD process.

In yet another aspect, there are provided precursor compositions for the deposition of a silicon containing film comprising:

an organoaminosilane having Formula A, B, and C or mixtures thereof:

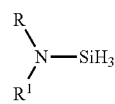

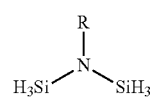

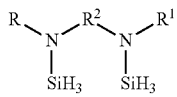

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group; and a solvent selected from the group consisting of an ether, a tertiary amine, a nitrile, an alkyl hydrocarbon, an aromatic hydrocarbon, a tertiary amino ether, or mixtures thereof. In one particular embodiment of the precursor compositions described herein, the organoaminosilane comprises a Formula A precursor wherein R is selected from a $C_5$ to $C_6$ cyclic alkyl group and $R^1$ is selected from the group consisting of linear or branched $C_1$ to $C_3$ alkyl group or a $C_5$ to $C_6$ cyclic alkyl group.

DETAILED DESCRIPTION OF THE INVENTION

Figure 1:
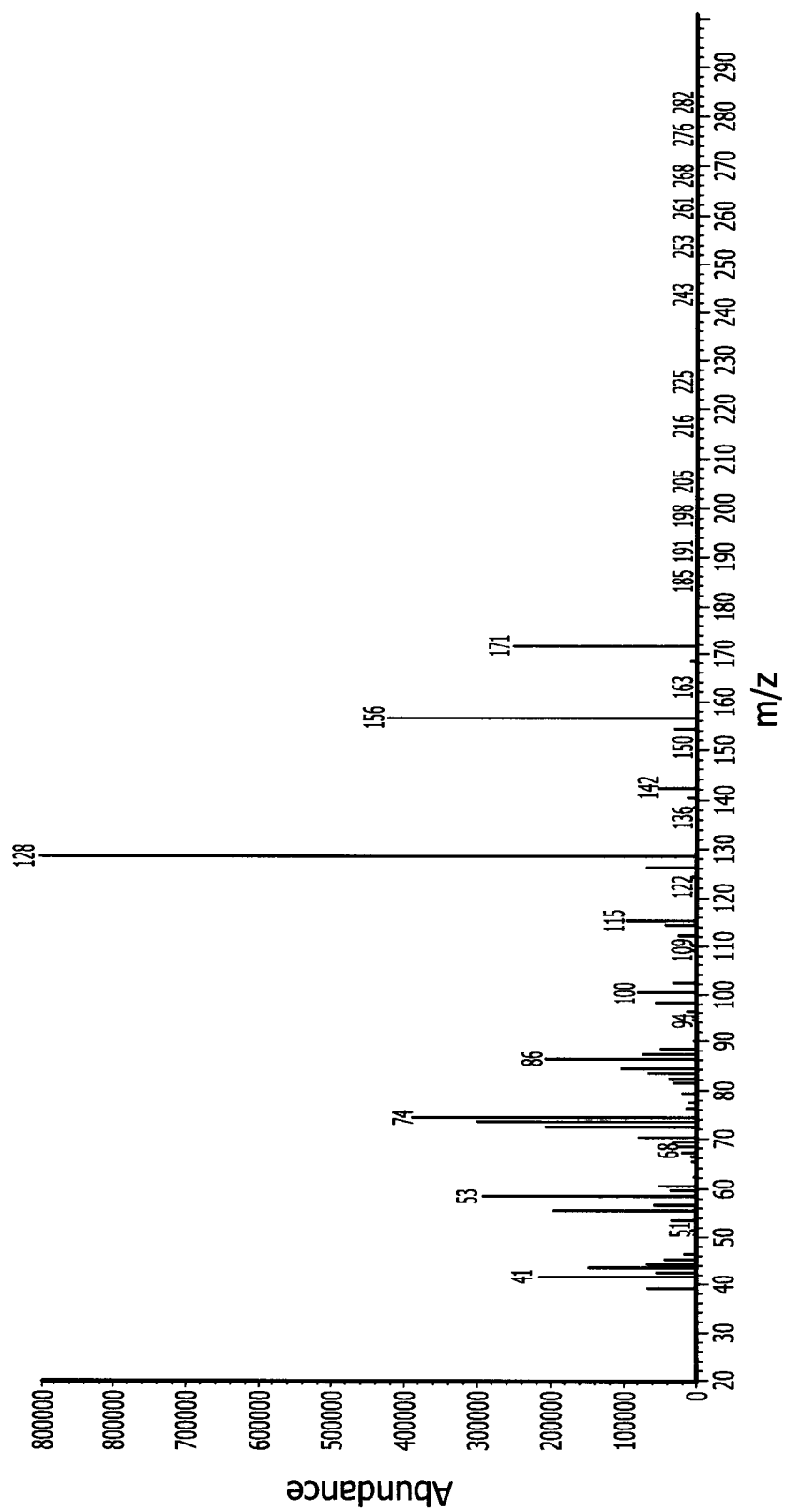
FIG. 1 provides the mass spectroscopy (MS) spectrum of N-iso-propylcyclohexylaminosilane having Formula A described herein and described in Table III no. 17 and in Example 1

Organoaminosilanes, silane, or silicon-containing precursors are used as precursors to form stoichiometric and non-stoichiometric silicon containing films such as, but not limited to, silicon oxide, silicon oxycarbide, silicon nitride, silicon oxynitride and silicon oxycarbonitride. These precursors can also be used, for example, as dopants for metal containing films. The organoaminosilane precursors are typically high purity volatile liquid precursor chemical that are vaporized and delivered to a deposition chamber or reactor as a gas to deposit a silicon containing film via CVD or ALD processes for semiconductor devices. The selection of precursor materials for deposition depends upon the desired resultant dielectric material or film. For example, a precursor material may be chosen for its content of chemical elements, its stoichiometric ratios of the chemical elements, and/or the resultant silicon containing film or coating that are formed under CVD. The precursor material may also be chosen for various other characteristics such as cost, relatively low toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

The organoaminosilanes precursors described herein exhibit a balance of reactivity and stability that makes them ideally suitable as CVD or ALD precursors. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor to prevent condensation or particles from forming in the container, lines, or both. With regard to stability, other organosilane precursors may form silane ($SiH_4$) as they degrade. Silane is pyrophoric at room temperature or it can spontaneously combust which presents safety and handling issues. Moreover, the formation of silane and other by-products decreases the purity level of the precursor and changes as small as 1 to 2% in chemical purity may be considered unacceptable for reliable semiconductor manufacture. In certain embodiments, the organoaminosilane precursors having Formulas A, B, or C described herein comprise less than 2% by weight, or less than 1% by weight, or less than 0.5% by weight of by-product (such as the corresponding bis-silane byproduct) after being stored for a 6 months or greater, or one year or greater time period which is indicative of being shelf stable. In addition to the foregoing advantages, in certain embodiments, such as for depositing a silicon oxide or silicon nitride film using an ALD or PEALD deposition method, the organoaminosilane precursor described herein may be able to deposit high density materials at relatively low deposition temperatures, e.g., 500° C. or less, or 400° C. or less, 300° C. or less, 200° C. or less, 100° C. or less, or 50° C. or less.

In one aspect, there is provided certain precursors or organoaminosilanes that are represented by the following formulas A, B, or C:

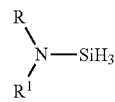

A

-continued

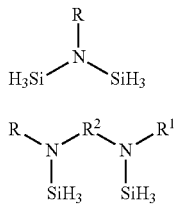

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group. In certain embodiments of Formula A, R and $R^1$ can be combined to form a cyclic or alkyl substituted cyclic group. In one particular embodiment, the organoaminosilane precursor is a compound having Formula A wherein R is a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In certain embodiments of the organoaminosilane of Formula A, $R^1$ and $R^2$ can be linked together to form a ring. In these or other embodiments, the ring comprises a heterocyclic ring. The ring, or alternatively, heterocyclic ring, may be saturated or unsaturated.

In alternative embodiments of the organoaminosilane of Formula A, $R^1$ and $R^2$ are not linked together to form a ring.

In certain embodiments of Formula C, any one or more of R, $R^2$, and $R^1$ can be combined to form a cyclic group. In these embodiments, the cyclic group may be a carbocyclic or heterocyclic group. The cyclic group can be saturated or, alternatively, unsaturated.

In other embodiments of Formula C, R and $R^1$ or any one or R, $R^2$, and $R^1$, respectively, are not combined to form a cyclic group.

In Formulas A, B, and C and throughout the description, the term "alkyl" denotes a linear, or branched functional group having from 1 to 20 or 1 to 10 or 3 to 10 or 1 to 6 carbon atoms. Exemplary linear alkyl groups include, but are not limited to, methyl, ethyl, propyl, butyl, pentyl, and hexyl groups. Exemplary branched alkyl groups include, but are not limited to, isopropyl, isobutyl, sec-butyl, tert-butyl, iso-pentyl, tert-pentyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto. The alkyl group may be saturated or, alternatively, unsaturated.

In Formulas A, B, and C and throughout the description, the term "cyclic alkyl" denotes a cyclic group having from 4 to 20 or 5 to 10 atoms. Exemplary cyclic alkyl groups include, but are not limited to, cyclobutyl, cyclopentyl, cyclohexyl, and cyclooctyl groups. In certain embodiments, the cyclic alkyl group may have one or more $C_1$ to $C_{10}$ linear, branched substituents, or substituents containing oxygen or nitrogen atoms. In this or other embodiments, the cyclic alkyl group may have one or more linear or branched alkyls or alkoxy groups as substituents, such as, for example, a methylcyclohexyl group or a methoxycyclohexyl group In Formulas A, B, and C and throughout the description, the term "aryl" denotes an aromatic cyclic functional group having from 5 to 10 carbon atoms or from 6 to 10 carbon atoms. Exemplary aryl groups include, but are not limited to, phenyl, benzyl, chlorobenzyl, tolyl, and o-xylyl.

In Formulas A, B, and C and throughout the description, the term "alkenyl group" denotes a group which has one or more carbon-carbon double bonds and has from 2 to 20 or from 2 to 10 or from 2 to 6 carbon atoms.

In Formulas A, B, and C and throughout the description, the term "alkoxy" denotes an alkyl group which has is linked to an oxygen atom (e.g., R—O) and may have from 1 to 20, or from 1 to 12, or from 1 to 6 carbon atoms. Exemplary alkoxy groups include, but are not limited to, methoxy (—$OCH_3$), ethoxy (—$OCH_2CH_3$), n-propoxy (—$OCH_2CH_2CH_3$), and iso-propoxy (—$OCHMe_2$).

In Formulas A, B, and C and through the description, the term "unsaturated" as used herein means that the functional group, substituent, ring or bridge has one or more carbon double or triple bonds. An example of an unsaturated ring can be, without limitation, an aromatic ring such as a phenyl ring. The term "saturated" means that the functional group, substituent, ring or bridge does not have one or more double or triple bonds.

In Formulas A, B, and C and throughout the description, the term "alkylamino group" denotes a group which has one or two alkyl groups attached to a nitrogen atom and has from 1 to 20 or from 2 to 12 or from 2 to 6 carbon atoms. An example of an alkylamino group can be, without limitation, a piperdine group.

In certain embodiments, one or more of the alkyl group, alkenyl group, alkynyl group, alkoxyalkyl group, alkoxy group, alkylaminoalkyl group, aryl group, and/or aromatic group in Formulas A, B, or C may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, alkoxyalkyl group, alkoxy group, alkylaminoalkyl group, aromatic and/or aryl group in Formulas A, B, or C may be unsubstituted.

In certain embodiments, the at least one organoaminosilane precursor having Formulas A, B, or C has one or more substituents comprising oxygen atoms. In these embodiments, the need for an oxygen source during the deposition process may be avoided. In other embodiments, the at least one organoaminosilane precursor having Formulas A, B, or C has one or more substituents comprising oxygen atoms also uses an oxygen source.

One class of silicon compound described herein is an organoaminosilane precursor and it is represented by formula A as follows:

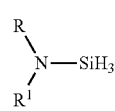

wherein R is independently selected from a $C_1$ to $C_{10}$ linear or branched, alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; $R^1$ is independently selected from a $C_3$-$C_{10}$ linear or branched, alkyl group; a $C_3$ to $C_{10}$ cyclic alkyl group; a $C_5$ to $C_{10}$ aromatic group; a $C_3$-$C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and wherein R and $R^1$ in Formula A are also combinable to form a cyclic group. In another embodiment of the organoaminosilane precursors having Formula A, R is an aromatic group with or without substituents and $R^1$ is a linear or branched alkyl group. In one particular embodiment of the compounds having Formula A, R is a $C_5$ to $C_6$ cyclic alkyl group and $R^1$ is selected from the group consisting of linear or branched $C_1$ to $C_3$ alkyl group or a $C_5$ to $C_6$ cyclic alkyl group.

In yet a further embodiment of Formula A, R and $R^1$ are combined to form a 5 or 6 member heterocyclic, substituted or unsubstituted, aromatic ring derived from one or more of the following, including but not limited to, pyrrole, alkyl substituted pyrrole, imidozale, alkyl substituted imidozale, pyrozale, or an alkyl-substituted pyrozale. Examples of such embodiments include, but are not limited to, N-silylpyrrole (Table III, no. 24), N-silyl-2,5-dimethypyrrole (Table III, no. 19), and 1-silyl-7-azaindole (Table III, no. 27).

In yet a further embodiment of Formula A, R and $R^1$ are combined to form a 5 or 6 member heterocyclic substituted or unsubstituted, aliphatic ring derived from one or more of the following, including but not limited to, pyrrolidine, piperidine, morpholine, piperrazine, or their alkyl-substituted derivatives. Examples of such embodiments include, but are not limited to, 2,6-dimethylmorpholinosilane (Table III, no. 10), 2-methylpyrrolidinosilane (Table III, no. 12), and N-silyldecahydroquinoline (Table III, no. 16).

In certain embodiments of Formula A, R and $R^1$ are the same substituents and the organoaminosilane is a symmetrical molecule with the proviso that both R and $R^1$ are not one of the following groups: ethyl, isopropyl, tert-butyl, isobutyl, sec-butyl, n-butyl, t-pentyl, and sec-pentyl groups. An example of such an embodiment includes, but is not limited to, dicyclohexylaminosilane (Table III, no. 7).

In other embodiments of Formula A, R and $R^1$ are different substituents and the organoaminosilane is an asymmetrical molecule. Examples of such embodiments include, but are not limited to, N-propyl-isopropylaminosilane (Table III, no. 4), N-methylcyclohexylaminosilane (Table III, no. 5), N-ethylcyclohexylaminosilane (Table III, no. 5), allylphenylaminosilane (Table III, no. 15), N-isopropylcyclohexylaminosilane (Table III, no. 17), allylcyclopentylaminosilane (Table III, no. 18), phenylcyclohexylaminosilane (Table III, no. 22), and 2-(N-silylmethylamino)pyridine (Table III, no. 25).

The second class of organoaminosilane precursor suited for use in producing silicon oxide layers is an organoaminosilane which has two silyl groups pendant from a single nitrogen atom as represented by formula B.

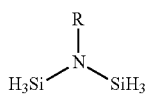

B

In Formula B, R is selected from a $C_6$ to $C_{10}$ substituted or unsubstituted aromatic group provided that R is not phenyl; a $C_3$ to $C_{10}$ substituted or unsubstituted cyclic alkyl group; a linear or a branched, substituted or unsubstituted $C_2$ to $C_6$ alkenyl group; a $C_1$ to $C_{10}$ alkoxyalkyl group; or a $C_1$ to $C_{10}$ alkylamino or dialkylamino group. R may also be a $C_4$ to $C_{10}$ linear or branched, substituted or unsubstituted alkyl group provided that R is not an unsubstituted tert-butyl, t-pentyl, or cyclohexyl group.

In certain embodiments of Formula B, R is a substituted $C_5$ to $C_{10}$ aromatic group wherein the aromatic group is substituted with one or more of the following: an alkyl group, an alkenyl group, an amino group, or an alkoxy group. Examples of such embodiments include without limitation N-(4-methoxyphenyl)disilazane (Table IV, no. 11), N-(3-methoxyphenyl)disilazane (Table IV, no. 12), N-(2-methoxyphenyl)disilazane (Table IV, no. 13), N-(4-chlorophenyl)disilazane (Table IV, no. 14), N-(2-chlorophenyl)disilazane (Table IV, no. 15), N-(2-ethylphenyl)disilazane (Table IV, no. 21), N-(2,6-diethylphenyl)disilazane (Table IV, no. 22), N-(2-propylphenyl)disilazane (Table IV, no. 23), N-(4-t-butylphenyl)disilazane (Table IV, no. 24), N-(4-iso-propylphenyl)disilazane (Table IV, no. 25), N-(2-iso-propylphenyl)disilazane (Table IV, no. 26), N-(3-ethylphenyl)disilazane (Table IV, no. 30), N-(4-sec-butylphenyl)disilazane (Table IV, no. 31), N-(4-vinyllphenyl)disilazane (Table IV, no. 32), N-(3-methylphenyl)disilazane (Table IV, no. 33), N-(4-methylphenyl)disilazane (Table IV, no. 34), N-(2,4,6-trimethylphenyl)disilazane (Table IV, no. 35), and N-(2,6-di-isopropylphenyl)disilazane (Table IV, no. 36).

In certain embodiments of Formula B, R is a $C_5$ to $C_{10}$ heterocyclic group wherein the heterocyclic group contains N or O atoms in the ring, and the group may be substituted with one or more of the following: an alkyl group, an alkenyl group, an amino group, or an alkoxy group. Examples of such embodiments include without limitation 1-N-(2-pyridyl)disilazane (Table IV, no. 1), N,N-disilyl-2-aminopyrimidine (Table IV, no. 2), N-(4-methyl-2-pyridyl)disilazane (Table IV, no. 16), N-(6-methyl-2-pyridyl)disilazane (Table IV, no. 17), N-(3-methyl-2-pyridyl)disilazane (Table IV, no. 18), N-(5-methyl-2-pyridyl)disilazane (Table IV, no. 19), and N-[2-(4-methylpyrimidino)amino]disilzane (Table IV, no. 37).

In certain embodiments of Formula B, R is a substituted $C_2$ to $C_{10}$ alkyl group wherein the alkyl group is substituted with one or more of the following: a hetero atom (e.g., N, Cl, O), an alkyl group, an aromatic group, an alkyl group, an alkylamino group, or an alkoxy group. Examples of such embodiments include without limitation N-t-pentyldisilazane (Table IV, no. 6), N-(2-dimethylamino-1-methylethyl)disilazane (Table IV, no. 7), N-(2-dimethylaminoethyl)disilazane (Table IV, no. 8), N-(1-cyclohexylethyl)disilazane (Table IV, no. 27), N,N-disilylcumylamine (Table IV, no. 29), N-[3,3-dimethylbuyl-2] disilazane (Table IV, no. 39), N,N-disilyl-2-picolylamine (Table IV, no. 40), N,N-disilyl-2-(2-pyridyl)ethylamine (Table IV, no. 41), and N,N-disilyl-1-(4-methylphenyl)ethylamine (Table IV, no. 42).

The third class of organoaminosilane compound is represented by formula C.

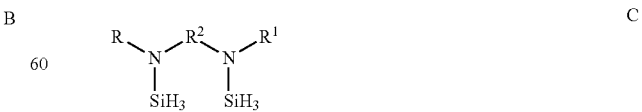

C

In Formula C, R is independently selected from a $C_1$ to $C_{10}$ linear or branched, alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$ to $C_{10}$ linear or branched, alkyl group; a $C_3$ to $C_{10}$ cyclic alkyl group; a $C_5$ to $C_{10}$ aromatic group; a $C_3$ to $C_{10}$ saturated or unsaturated carbocyclic or heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched hydrocarbon chain wherein the number of carbon atoms ranges from 1 to 10; a saturated or unsaturated, carbocyclic or heterocyclic ring; $SiR_2$; or $SiH_2$. In certain embodiments, R and $R^1$ are the same. In alternative embodiments, R and $R^1$ are different. The $R^2$ group bridges the nitrogen atoms. In embodiments wherein the $R^2$ group is a single bond, it can be the N atom bonded directly to the N atom in the compound. In certain embodiments, the $R^2$ group is nothing more than a single bond between the nitrogen atoms. In an alternative embodiment, the $R^2$ group it may be a bridging group, such as $SiR_2$, $SiH_2$, a chain, a ring, or a $C_1$-$C_{10}$ linear or a $C_3$-$C_{10}$ branched alkyl. In a further embodiment of Formula C, R and $R^1$ can be linked together. In the later embodiment, R and $R^1$ in Formula C can be combined into a heterocyclic group via formation of a single or a double carbon-carbon bond or a linkage through oxygen or nitrogen atom.

Without being bound by theory, it is believed that organoaminosilane precursors such as those organoaminosilanes having formulas A, B, and C described herein and having one or more —$SiH_3$ groups are advantageous over other organoaminosilane precursors containing $SiH_2$ or —SiH groups because of its lower activation barrier to react on a hydroxylated semi-conductor surface (thus lower deposition temperature), lower impurity and higher film density after deposition. However, certain organoaminosilane precursors having a —$SiH_3$ group such as dimethylaminosilane (DMAS) or diethylaminosilane (DEAS) are not be thermally stable because it undergoes a disproportionation reaction to form pyrophoric silane and bis(dimethylamino)silane or bis(diethylamino)silane, respectively. Further, it is thought that films deposited using these particular organoaminosilane precursors may contain appropriate levels and types of carbon in silicon nitride or silicon carbonitride networks that may enable a significant reduction in wet etch rate yet maintaining a certain dielectric constant value.

In certain embodiments, the organoaminosilanes having Formulas A, B, or C can be prepared by reacting a monohalidosilane ($XSiH_3$ wherein X=Cl, Br, or I) or lower molecular dialkylaminosilane such as di-iso-propylaminosilane with one or more of the following amines provided in Tables I (Formula A) and II (Formulas B and C) in an organic solvent or solvent mixture.

TABLE I

Amines to be used in Synthesis of Formula A precursors

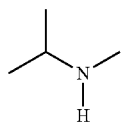

N-methylisopropylamine

TABLE I-continued

Amines to be used in Synthesis of Formula A precursors

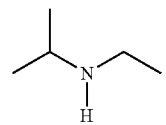

N-ethylisopropylamine

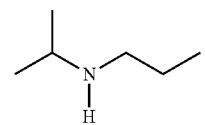

N-propylisopropylamine

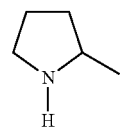

2-methylpyrrolidine

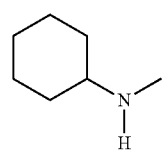

N-methylcyclohexylamine

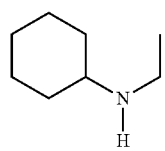

N-ethylcyclohexylamine

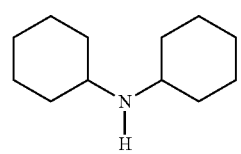 [SMILES: C1CCC(NC2CCCCC2)CC1]

Dicyclohexylamine

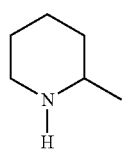

2-methylpiperidine

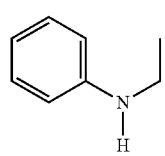

N-ethylaniline

TABLE I-continued

Amines to be used in Synthesis of Formula A precursors

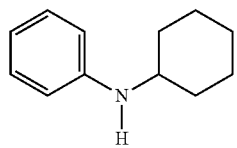 [SMILES: c1ccc(NC2CCCCC2)cc1]

N-cyclohexylaniline

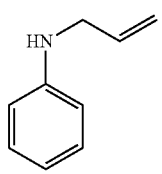

N-allylaniline

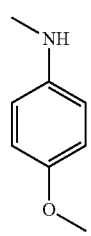

N-methyl-p-anisidine

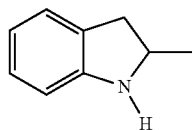

2-methylindoline

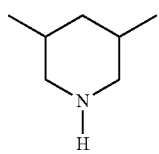

3,5-dimethylpiperdine

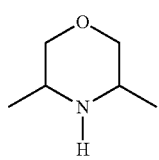

2,6-Dimethylmorphline

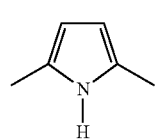

2,5-Dimethylpyrrole

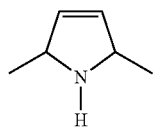

2,5-Dimethyl-3-pyrroline

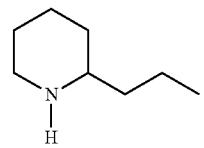

conline

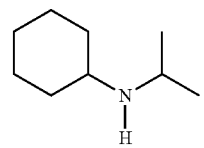

N-iso-propylcyclohexylamine

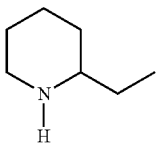

2-ethylpiperidine

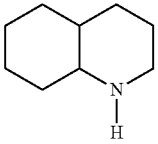

Decahydroquinoline

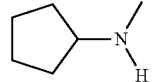

Cyclopentylmethylamine

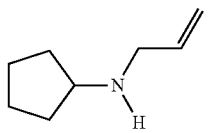

N-allylcyclopentylamine

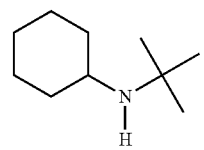

N-t-butylcyclohexylamine

TABLE II

Amines to be used in Synthesis of Formula B or C precursors iso-propylamine tert-butylamine tert-pentylamine 1-adamantylanime

Cyclopropylamine cyclobutylamine

Cyclopentylamine

Cyclohexylamine

TABLE II-continued

Amines to be used in Synthesis of Formula B or C precursors cycloheptylamine

Cyclooctylamine

Aniline 2-methylaniline 3-methylaniline 4-methylaniline 2-ethylaniline

TABLE II-continued

Amines to be used in Synthesis of Formula B or C precursors 3-ethylaniline 4-ethylaniline 2,5-dimethylpiperazine 1,2-phenylenediamine 1,4-phenylenediamine 1,4-phenylenediamine 1,2-diaminocyclohexane 1,3-diaminocyclohexane 1,4-diaminocyclohexane 1-dimethylamino-2-propylamine N,N-dimethylethylenediamine 1-methoxy-2-propylamine 2-aminoimidazole 2-aminopyridine 2-aminopyrimidine The following Equations (1) through (6) provide examples of reaction schemes or synthesis routes which may be used to make the organoaminosilanes having Formula A, B, or C as described herein. In Equations (1) through (6), substituents R, $R^1$, and $R^2$ are the same as those described herein for Formulas A, B, or C; M is Li, N, or K; and X is Cl, Br, or I; R' in equation (5) is selected from a $C_1$ to $C_{10}$ linear or branched, alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group;

a $C_1$ to $C_{10}$ alkoxy group; a $C_1$ to $C_{10}$ alkylamino group. In addition, $R'_3N$ can also employed in equation (2) to form $R'_3N$—HCl instead of $RR^1N$—HCl to reduce the amount of $RR^1NH$ being used. Reaction schemes in Equations (1) through (6) can be conducted with (e.g., in the presence of) or without organic solvents. In embodiments wherein an organic solvent is used, examples of suitable organic solvents include, but are not limited to, hydrocarbon such as hexanes, octane, toluene, and tetrahydrofuran (THF). In these or other embodiments, the reaction temperature is in the range of from about −70° C. to the boiling point of the solvent employed if a solvent is involved. The resulting organoaminosilane can be purified via vacuum distillation after removing all by-products as well as solvent(s) if present. Equations (1) through (5) are different embodiments for making precursors having Formulas A or B. Eq. (5) is a modification of Eq. (2) to make it more suitable for Formula B compounds. Eq. (6) represents the synthesis method for Formula C.

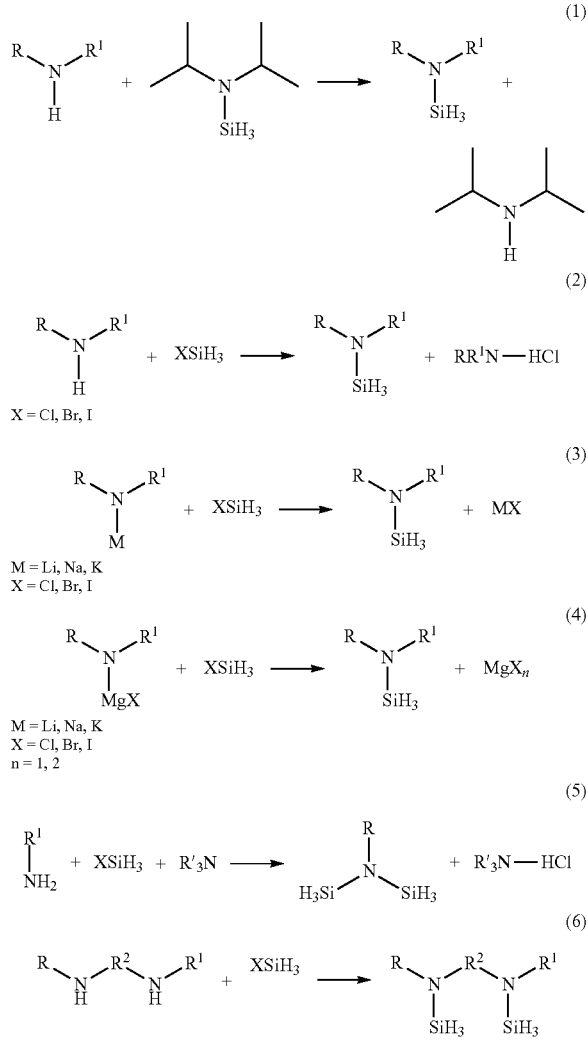

The method used to form the silicon-containing silicon containing films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the silicon containing film is deposited using an ALD process. In another embodiment, the silicon containing film is deposited using a CCVD process. In a further embodiment, the silicon containing film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the silicon containing film. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

As previously mentioned, in certain embodiments, such as for depositing a silicon oxide or silicon nitride film using an ALD or PEALD deposition method, the organoaminosilane precursor having Formula A, B, or C described herein may be able to deposit films at relatively low deposition temperatures, e.g., of 500° C. or less, or 400° C. or less, 300° C. or less, 200° C. or less, 100° C. or less, or 50° C. or less or room temperature. In these or other embodiments, the substrate (deposition) temperature ranges from, the difference between the boiling points ranges from any one or more of the following end-points: 25, 50, 100, 200, 300, 400, or 500° C. Examples of these ranges are, without limitation, 25 to 50° C., 100° to 300° C., or 100° C. to 500° C.

In certain embodiments, the method described herein further comprises one or more additional silicon-containing precursors other than the organoaminosilane precursor having the above Formulas A, B, or C. Examples of additional silicon-containing precursors include, but are not limited to, organo-silicon compounds such as siloxanes (e.g., hexamethyl disiloxane (HMDSO) and dimethyl siloxane (DMSO)); organosilanes (e.g., methylsilane; dimethylsilane; vinyl trimethylsilane; trimethylsilane; tetramethylsilane; ethylsilane; disilylmethane; 2,4-disilapentane; 1,4-disilabutane; 2,5-disilahexane; 2,2-disilylpropane; 1,3,5-trisilacyclohexane, and fluorinated derivatives of these compounds; phenyl-containing organo-silicon compounds (e.g., dimethylphenylsilane and diphenylmethylsilane); oxygen-containing organo-silicon compounds, e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing and/or organoaminosilane precursor may be introduced into the reactor for a predetermined time period. In certain embodiments, the time period ranges from about 0.001 to about 500 seconds.

In certain embodiments, the silicon containing films deposited using the methods described herein is formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), water plasma, oxygen ($O_2$), peroxide ($O_3$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited silicon containing film.

In certain embodiments, the silicon containing films comprise silicon and nitrogen. In these embodiments, the silicon containing films deposited using the methods described herein are formed in the presence of nitrogen-containing source. A nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting silicon containing film.

Energy is applied to the at least one of the precursor, nitrogen-containing source, reducing agent, other precursors or combination thereof to induce reaction and to form the silicon containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminosilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations or compositions, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the precursor(s) having Formula A, B, or C is used in a composition comprising a solvent and an organoaminosilane precursor having Formula A, B, or C described herein, the solvent or mixture thereof selected does not react with the organoaminosilane. The amount of solvent by weight percentage in the composition ranges from 0.5% by weight to 99.5% or from 10% by weight to 75%. In this or other embodiments, the solvent has a boiling point (b.p.) similar to the b.p. of the organoaminosilane of Formula A, B, or C or the difference between the b.p. of the solvent and the b.p. of the organoaminosilane of Formula A, B, or C is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof. Some non-limiting exemplary compositions include, but not limited to, a composition comprising di-iso-propylaminosilane (b.p. about 116° C.) and octane (b.p. 125 to 126° C.); di-iso-propylaminosilane (b.p. about 116° C.) and pyridine (b.p. 115° C.); di-iso-propylaminosilane (b.p. about 116° C.) and toluene (b.p. 110° C.); a composition comprising N-methylcyclohexylaminosilane (b.p. about 171° C. and decane (b.p. 174° C.); a composition comprising N-methylcyclohexylaminosilane (b.p. about 171° C. and diethylene glycol dimethyl ether (b.p. 162° C.); a composition comprising N-iso-propylcyclohexylaminosilane (b.p. about 199° C.) and bis(2-dimethylaminoethyl)ether (b.p., 189° C.); N-iso-propylcyclohexylaminosilane (b.p. about 199° C.) and benzonitrile (b.p., 191° C.).

In another embodiment, a vessel for depositing a silicon containing film comprising one or more organoaminosilane precursor having Formulas A, B, or C is described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the organoaminosilane precursor of Formulas A, B, or C is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the organoaminosilane precursor and/or other precursor can be maintained in separate vessels or in a single vessel having separation means for maintaining the organoaminosilane precursor and other precursor separate during storage.

As previously mentioned, the purity level of the organoaminosilane is sufficiently high enough to be acceptable for reliable semiconductor manufacturing. In certain embodiments, the organoaminosilane precursors having formulas A, B, or C described herein comprise less than 2% by weight, or less than 1% by weight, or less than 0.5% by weight of one or more of the following impurities: free amines, halides, and higher molecular weight species. Higher purity levels of the organoaminosilanes described herein can be obtained through one or more of the following processes: purification, adsorption, and/or distillation.

In one embodiment of the method described herein, a cyclic deposition process such as CCVD, ALD, or PEALD may be employed, wherein at least one silicon-containing precursor selected from an organoaminosilane precursor having Formulas A, B, or C and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

In certain embodiments of the method described herein, a reducing agent is used in the deposition process. Examples of reducing agents include, but are not limited to, hydrogen, hydrazine, or hydrogen plasma.

In certain embodiments, the gas lines connecting from the precursor canisters to the reaction chamber are heated to one or more temperatures depending upon the process requirements and the container of the organoaminosilane precursor having Formulas A, B, or C is kept at one or more temperatures for bubbling. In other embodiments, a solution comprising the at least one silicon-containing precursor having Formulas A, B, or C is injected into a vaporizer kept at one or more temperatures for direct liquid injection.

A flow of argon and/or other gas may be employed as a carrier gas to help deliver the vapor of the at least one organoaminosilane precursor to the reaction chamber during the precursor pulsing. In certain embodiments, the reaction chamber process pressure is about 1 Torr.

In a typical ALD or CCVD process, the substrate such as a silicon oxide substrate is heated on a heater stage in a reaction chamber that is exposed to the silicon-containing precursor initially to allow the complex to chemically adsorb onto the surface of the substrate.

A purge gas such as argon purges away unabsorbed excess complex from the process chamber. After sufficient purging, a nitrogen-containing source may be introduced into reaction chamber to react with the absorbed surface followed by another gas purge to remove reaction by-products from the chamber. The process cycle can be repeated to achieve the desired film thickness.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon containing film.

In another embodiment of the method disclosed herein, the films containing both silicon and nitrogen are formed using a ALD deposition method that comprises the steps of:
    providing a substrate in an ALD reactor;
    introducing into the ALD reactor an at least one organoaminosilane having Formula A, B, and C or mixtures thereof:

-continued

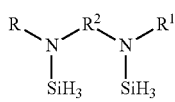

C wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group;

chemisorbing the at least one organoaminosilane precursor onto a substrate;

purging away the unreacted at least one organoaminosilane precursor using a purge gas;

providing a nitrogen-containing source to the organoaminosilane precursor onto the heated substrate to react with the sorbed at least one organoaminosilane precursor; and optionally purging away any unreacted nitrogen-containing source.

In another embodiment of the method disclosed herein, the silicon containing films is formed using a ALD deposition method that comprises the steps of:

providing a substrate in a reactor;

introducing into the reactor an at least one organoaminosilane having Formula A, B, and C or mixtures thereof:

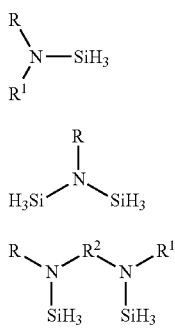

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group;

chemisorbing the at least one organoaminosilane precursor onto a substrate;

purging away the unreacted at least one organoaminosilane precursor using a purge gas;

providing an oxygen source to the organoaminosilane precursor onto the heated substrate to react with the sorbed at least one organoaminosilane precursor; and optionally purging away any unreacted oxygen source.

In a further embodiment of the method described herein, the organoaminosilane precursors are used for depositing a silicon containing film which is an amorphous film, a crystalline silicon film, or a mixture thereof. In these embodiments, the silicon containing films is formed using a deposition method selected from ALD or cyclic CVD that comprises the steps of:

placing a substrates into a reactor which is heated to a temperature ranging from ambient temperature to about 700° C. and maintained at a pressure of 1 Torr or less;

introducing into the reactor an at least one organoaminosilane having Formula A, B, and C or mixtures thereof:

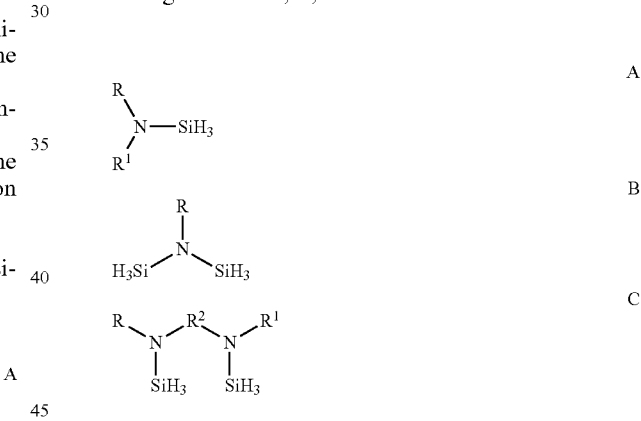

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group;

providing a reducing agent into the reactor to at least partially react with the at least one organoaminosilane precursor and deposit a silicon containing film onto the one or more substrates wherein the reducing agent is at least one selected from the group consisting of hydrogen, hydrogen plasma, or hydrogen chloride.

The above steps define one cycle for the method described herein; and the cycle can be repeated until the desired thickness of a silicon containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting silicon containing film, although always using oxygen in less than a stoichiometric amount relative to the available silicon.

For multi-component silicon containing films, other precursors such as silicon-containing precursors, nitrogen-containing precursors, reducing agents, or other reagents can be alternately introduced into the reactor chamber.

In a further embodiment of the method described herein, the silicon containing film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing at least one organoaminosilane having Formula A, B, and C or mixtures thereof:

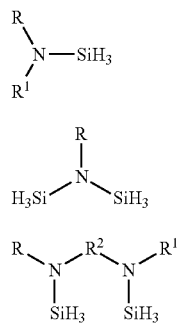

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group; and providing an oxygen source into the reactor to at least partially react with the at least one organoaminosilane precursor and deposit the silicon containing film onto the one or more substrates. In certain embodiments of the CVD method, the reactor is maintained at a pressure ranging from 100 mTorr to 600 mTorr during the introducing step.

The above steps define one cycle for the method described herein; and the cycle can be repeated until the desired thickness of silicon containing film the silicon containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting silicon containing film, although always using oxygen in less than a stoichiometric amount relative to the available silicon.

For multi-component silicon containing films, other precursors such as silicon-containing precursors, nitrogen-containing precursors, oxygen sources, reducing agents, and/or other reagents can be alternately introduced into the reactor chamber.

In a further embodiment of the method described herein, the silicon containing film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing at least one organoaminosilane having Formula A, B, and C or mixtures thereof is employed as at least one of the silicon containing precursors:

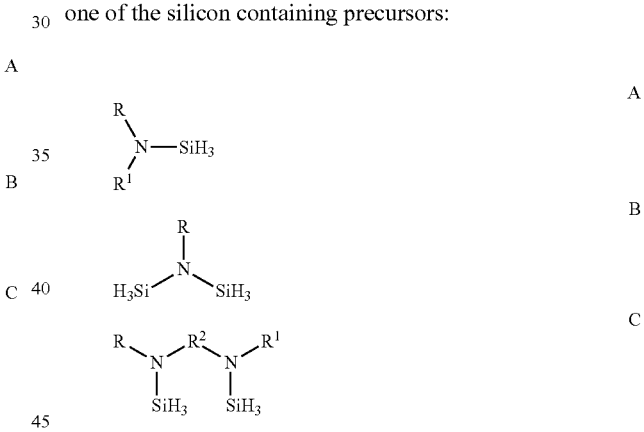

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_2$ to $C_{10}$ alkenyl group; a $C_1$ to $C_{10}$ alkoxy group; a $C_1$ to $C_{10}$ alkylamino group; or a silyl group in formula C with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_2$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group; and providing a nitrogen-containing source into the reactor to at least partially react with the at least one organoaminosilane precursor and deposit a silicon containing film onto the one or more substrates. In certain embodiments of the CVD method, the reactor is maintained at a pressure ranging from 100 mTorr to 600 mTorr during the introducing step.

In certain embodiments, the organoaminosilane precursors having Formulas A, B, or C described herein can also be used a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino) hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino) bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metal herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W.

In certain embodiments, the resultant silicon containing films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the silicon containing films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or silicon containing film that is formed using the organoaminosilane precursors and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to about 50%; and H ranges from about 0% to about 50% atomic percent weight % wherein x+y+z+v+w=100 atomic weight percent, as determined for example, by XPS or other means.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), and liquid crystal displays (LCD).

The following examples illustrate the method for preparing organoaminosilane precursors as well as deposited silicon-containing films described herein and are not intended to limit it in any way.

EXAMPLES

Example 1

Synthesis of N-isopropylcyclohexylaminosilane and Other Organoaminosilane Precursors Having Formula A In a 500 ml Schlenk flask 247.3 g (1.75 mol) N-isopropylcyclohexylamine and 229.9 g (1.75 mol) di-isopropylaminosilane were refluxed for 8 days under nitrogen. The byproduct di-isopropylamine was removed with vacuum at a pressure of 40 mmHg and 50° C. Fractional vacuum distillation provided 50 g of pure N-isopropylcyclohexylaminosilane. The normal boiling point (measured at 1 atmosphere) is about 199° C. measured by differential scanning calorimetry (DSC). The end-product was characterized by mass spectroscopy (MS) which is provided in FIG. 1 with peaks at 171 (M+), 156 (M-$CH_3$).

Two 10 cc stainless steel ampoules were carefully washed and baked out at 175° C. prior to use. Five gram samples of N-isopropylcyclohexylamine were individually loaded in the ampoules inside glove box. The ampoules were then stored in constant temperature environments using laboratory ovens pre-set at 80° C.±2° C. for one week and two-week intervals. The samples were evaluated by gas chromatography (GC) to determine the extent of degradation. The GC results showed that the assay only dropped about 0.20 wt % for one week and 0.27 wt % for two weeks, demonstrating it has excellent stability and can be employed as a suitable precursor for reliable semi-conductor processes.

Additional organoaminosilane precursors of Formula A were made in accordance with the reaction scheme described herein in Equation (1) using di-iso-propylaminosilane and one or more of the following amines provided in Table I. The desired organoaminosilane precursors having Formula A were obtained by vacuum distillation and characterized by mass spectroscopy (MS). The molecular weight (MW), the structure, and corresponding MS fragmentation peaks of each organoaminosilane precursor are provided in Table III to confirm their identification.

TABLE III
| | Organoaminosilanes Having Formula A | | | |
|---|---|---|---|---|
| No. | Precursor Name | MW | Structure | MS Peaks |
| 1 | Di-sec-butylaminosilane | 159.34 | 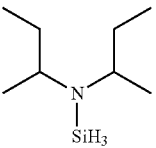 | 159, 144, 130, 102, 88, 74 |
| 2 | Phenylmethylaminosilane | 137.25 | 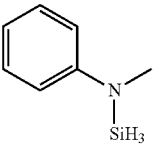 | 137, 136, 122, 119, 106, 93, 77 |
| 3 | 2,6-dimethylpiperidinosilane | 143.30 | 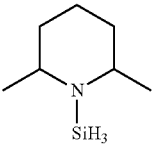 | 143, 128, 112, 100, 86, 72, 58 |
| 4 | N-propyl-iso-propylaminosilane | 131.29 | 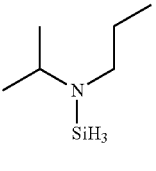 | 131, 116, 88, 74, 58, 43 |
| 5 | N-methylcyclohexylaminosilane | 143.30 | 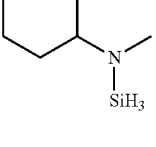 | 143, 142, 128, 114, 100, 87, 70 |
| 6 | N-ethylcyclohexylaminosilane | 157.33 | 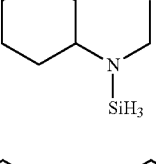 | 157, 142, 128, 114, 101, 84, 73, 58 |
| 7 | Dicyclohexylaminosilane | 211.52 | 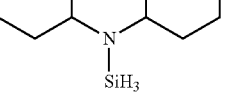 | 211, 168, 140, 86, 73 |
| 8 | 2-Methylpiperidinosilane | 129.28 | 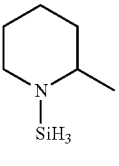 | 129, 114, 98, 86, 72, 58 |
| 9 | N-silyl-2-methylindoline | 163.29 | 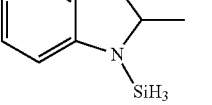 | 163, 148, 132, 117, 105, 91, 77 |

TABLE III-continued

Organoaminosilanes Having Formula A

| No. | Precursor Name | MW | Structure | MS Peaks |
|---|---|---|---|---|
| 10 | 2,6-Dimethylmorpholinosilane | 145.27 | 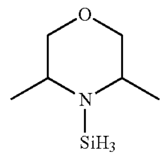 | 145, 130, 114, 100, 59 |
| 11 | 3,5-dimethylpiperidinosilane | 143.30 | 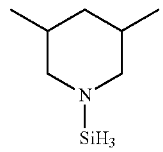 | 143, 142, 138, 112, 100, 86, 74 |
| 12 | 2-Methylpyrrolodinosilane | 115.24 | 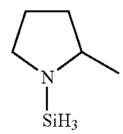 | 115, 114, 100, 86, 72 |
| 13 | N-methyl-iso-propylaminosilane | 103.24 | 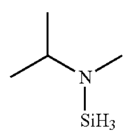 | 103, 85, 72, 58 |
| 14 | N-ethyl-iso-propylaminosilane | 117.26 | 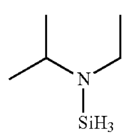 | 117, 116, 102, 84, 72, 60 |
| 15 | Allylphenylaminosilane | 163.92 | 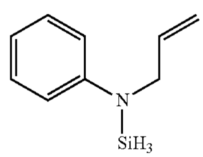 | |
| 16 | N-silyldecahydroquinoline | 169.34 | 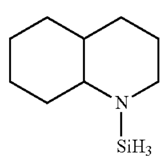 | 169, 154, 138, 126, 112, 96, 74 |
| 17 | N-isopropylcyclohexylaminosilane | 171.36 | 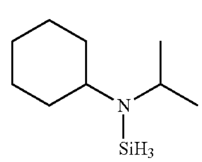 | 171, 156, 128, 115, 86, 74 |
| 18 | Allylcyclopentylaminosilane | 155.31 | 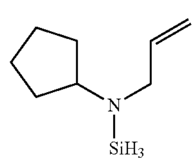 | 155, 140, 126, 114, 98, 96, 84, 68 |
| 19 | N-silyl-2,5-dimethylpyrrole | 125.07 | 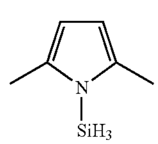 | 125, 124, 110, 94, 83, 69, 55 |

TABLE III-continued

Organoaminosilanes Having Formula A

| No. | Precursor Name | MW | Structure | MS Peaks |
|-----|----------------|------|-----------|----------|
| 20 | Phenylethylaminosilane | 151.28 | 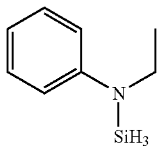 | 151, 136, 120, 104, 93, 77 |
| 21 | N-iso-propylethylaminosilane | 117.26 | 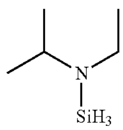 | 117 (M+), 102 (M − H), 86 (M − SiH3), 72, 60 |
| 22 | Phenylcyclohexylaminosilane | 205.37 | 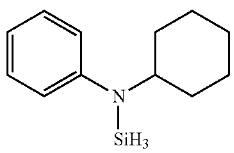 | 205, 175, 162, 132, 118, 106, 93, 77 |
| 23 | 2,2,6,6-tetramethylpiperidinosilane | 171.36 | 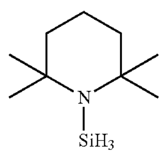 | 171, 156, 126, 109, 100, 88, 69 |
| 24 | N-silylpyrrole | 97.19 | 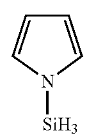 | 97, 82, 70, 55 |
| 25 | 2-(N-silylmethylamino)pyridine | 138.24 | 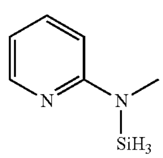 | 138, 121, 107, 94, 80, 67 |
| 26 | Phenyl-iso-propylaminosilane | 165.31 | 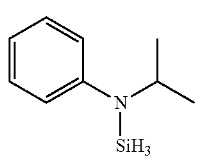 | 165, 150, 135, 120, 103, 93, 77 |
| 27 | 1-silyl-7-azaindole | 148.24 | 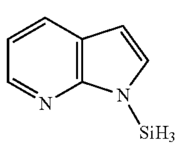 | 148, 147, 133, 118, 91 |

Example 2

Synthesis of N-2-pyridyldisilazane and Other Organoaminosilane Precursors Having Formula B In a 500 ml Schlenk flask, 57 (0.5 mol) 2-aminopyridine and 196.5 g (1.5 mol) di-isopropylaminosilane were stirred at ambient temperature under a nitrogen atmosphere for 12 hours. The relatively lower boiling point byproduct di-isopropylamine was removed with vacuum at a pressure of 20 mmHg and room temperature (25° C.). The reaction mixture was then stirred for another 12 hours. The product N-2-pyridyldisilazane (65 g, 84.5% yield) was obtained by vacuum distillation with boiling point of 60° C. at 6 mm Hg. The end-product was characterized by mass spectroscopy (MS) which is provided in FIG. 1 and shows, among other things, peaks at 154 (M+), 153 (M-CH$_3$), 123 (M-SiH$_3$), 121, 106, 94, and 80. The molecular weight of the N-2-pyridyldisilazane was 154.32.

Additional organoaminosilane precursors were made in accordance with the reaction scheme described herein in Equation (5) using di-iso-propylaminosilane and one or more of the following amines provided in Table II (Formula B) to provide a reaction mixture and the reaction mixture is stirred at ambient temperature under a nitrogen atmosphere for 12 hours. The choice of amine selected influenced the desired resulting end-product precursor. For example, N-adamantyl-disilazane was made from a reaction mixture comprising di-iso-propylaminosilane and 1-adamantylamine. The relatively lower boiling point byproduct di-isopropylamine was removed with vacuum at a pressure of 20 mmHg and room temperature (25° C.). The reaction mixture was then stirred for another 12 hours. The desired organoaminosilane end-product having Formula B was obtained by vacuum distillation. The end-product was characterized by mass spectroscopy (MS) and the peaks and molecular weight for each end-product are provided in Table IV to confirm their identification.

TABLE IV

Organoaminosilanes Having Formula B

| No. | Precursor Name | MW | Structure | MS Peaks |
|---|---|---|---|---|
| 1 | N-(2-pyridyl)disilazane | 154.32 | 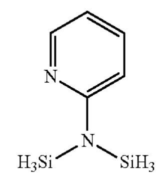 | 154, 153, 123, 121, 106, 94, 80 |
| 2 | N,N-disilyl-2-aminopyrimidine | 155.31 | 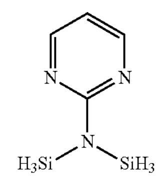 | 155, 154, 124, 122, 98, 70 |
| 3 | N-cyclopropyldisilazane | 117.04 | 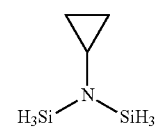 | 117, 116, 102, 86, 72 |
| 4 | N-cyclopentylldisilazane | 145.35 | 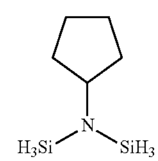 | 145, 144, 130, 116, 88, 72 |
| 5 | N-cycloheptyldisilazane | 143.20 | 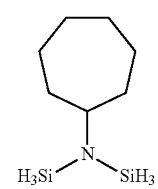 | 143, 142, 114, 100, 86, 72 |
| 6 | N-t-pentyldisilazane | 147.36 | 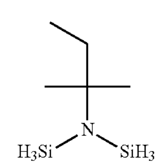 | 147, 146, 132, 118, 100, 86, 72 |
| 7 | N-(2-dimethylamino-1-methylethyl)disilazane | 162.38 | 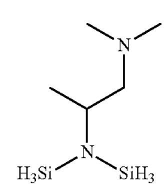 | 162, 161, 144, 129, 116, 104, 86, 77 |

TABLE IV-continued

Organoaminosilanes Having Formula B

| No. | Precursor Name | MW | Structure | MS Peaks |
|-----|----------------|-----|-----------|----------|
| 8 | N-(2-dimethylaminoethyl)disilazane | 148.35 | (structure) | 148, 147, 131, 117, 102, 90, 72 |
| 9 | N-cyclobutylaminosilane | 131.32 | (structure) | 131, 116, 103, 88, 72 |
| 10 | N-adamantyldisilazane | 211 | (structure) | 211, 154, 117, 94, 79 |
| 11 | N-(4-methoxyphenyl)disilazane | 153.25 | (structure) | 153, 138, 120, 108, 92, 80 |
| 12 | N-(3-methoxyphenyl)disilazane | 153.25 | (structure) | 153, 138, 122, 108, 93, 78 |
| 13 | N-(2-methoxyphenyl)disilazane | 153.25 | (structure) | 153, 137, 120, 108, 92, 77 |
| 14 | N-(4-chlorophenyl)disilazane | 187.77 | (structure) | 187, 155, 118, 112, 93, 77, 63 |
| 15 | N-(2-chlorophenyl)disilazane | 187.77 | (structure) | 187, 150, 120, 108, 93, 79 |

TABLE IV-continued

| | | Organoaminosilanes Having Formula B | | |
|---|---|---|---|---|
| No. | Precursor Name | MW | Structure | MS Peaks |
| 16 | N-(4-methyl-2-pyridyl)disilazane | 168.34 | | 168, 167, 135, 120, 108 |
| 17 | N-(6-methyl-2-pyridyl)disilazane | 168.34 | | 168, 167, 135, 120, 108 |
| 18 | N-(3-methyl-2-pyridyl)disilazane | 168.94 | | 168, 167, 135, 120, 108 |
| 19 | N-(5-methyl-2-pyridyl)disilazane | 168.94 | | 168, 167, 135, 120, 110 |
| 20 | N-piperidinodisilazane | 160.36 | | 160, 129, 117, 103, 84, 74 |
| 21 | N-(2-ethylphenyl)disilazane | 181.38 | | 181, 151, 136, 120, 104, 93, 74 |
| 22 | N-(2,6-diethylphenyl)disilazane | 209.44 | | 207, 192, 178, 162, 148, 132, 120, 105, 91 |
| 23 | N-(2-propylphenyl)disilazane | 195.41 | | 195, 166, 106, 91 |

TABLE IV-continued

Organoaminosilanes Having Formula B

| No. | Precursor Name | MW | Structure | MS Peaks |
|---|---|---|---|---|
| 24 | N-(4-t-butylphenyl)disilazane | 209.11 | 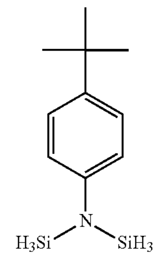 | 209, 194, 179, 164, 149, 134, 122, 106, 91 |
| 25 | N-(4-iso-propylphenyl)disilazane | 195.41 | 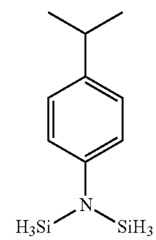 | 195, 180, 148, 120, 105, 91 |
| 26 | N-(2-iso-propylphenyl)disilazane | 195.41 | 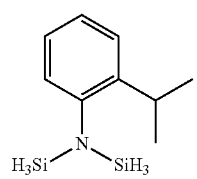 | 195, 180, 148, 135, 120, 105, 91 |
| 27 | N-(1-cyclohexylethyl)disilazane | 187.43 | 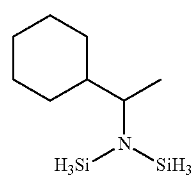 | 186, 170, 90, 72 |
| 28 | N,N-disilyl-1-aminopyrrole | 142.31 | 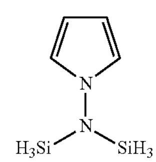 | 142, 127, 114, 98 |
| 29 | N,N-disilylcumylamine | 195.09 | 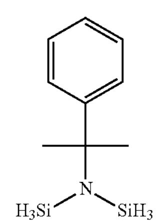 | 195, 180, 162, 148, 117, 103, 91 |
| 30 | N-(3-ethylphenyl)disilazane | 181.39 | 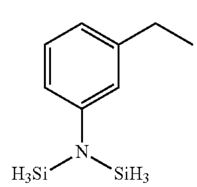 | 181, 166, 152, 132, 120, 106, 91 |

TABLE IV-continued

Organoaminosilanes Having Formula B

| No. | Precursor Name | MW | Structure | MS Peaks |
|---|---|---|---|---|
| 31 | N-(4-sec-butylphenyl)disilazane | 209.44 | 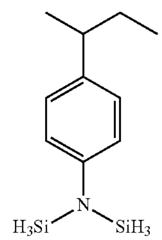 | 209, 193, 179, 164, 150, 134, 120, 105, 91, 77 |
| 32 | N-(4-vinyllphenyl)disilazane | 179.37 | 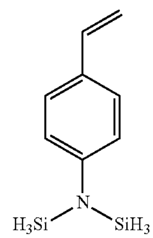 | 179, 164, 147, 132, 120, 104, 91 |
| 33 | N-(3-methylphenyl)disilazane | 167.36 | 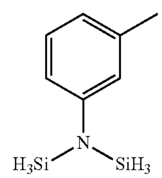 | 167, 152, 135, 119, 107, 92 |
| 34 | N-(4-methylphenyl)disilazane | 167.36 | 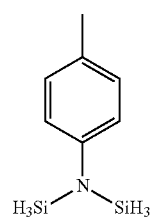 | 167, 152, 135, 119, 107, 92 |
| 35 | N-(2,4,6-trimethylphenyl)disilazane | 195.31 | 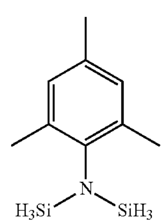 | 195, 180, 162, 148, 134, 120, 105, 91 |
| 36 | N-(2,6-di-iso-pripylphenyl)disilazane | 237.49 | 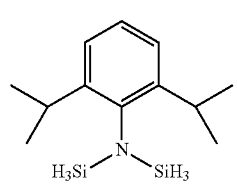 | 237, 219, 204, 176, 132, 120, 106, 91 |
| 37 | N-[2-(4-methylpyrimidino)amino]disilazane | 169.33 | 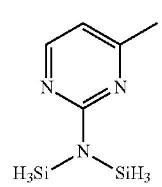 | 169, 168, 154, 136, 112, 101 |

TABLE IV-continued

Organoaminosilanes Having Formula B

| No. | Precursor Name | MW | Structure | MS Peaks |
|---|---|---|---|---|
| 38 | 1,1-disilyl-2-methyl-2-phenylhydrazine | 182.39 | 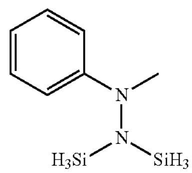 | 182, 163, 149, 134, 107, 77 |
| 39 | N-(3,3-dimethylbutyl-2)disilazane | 161.37 | 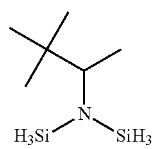 | 160, 158, 146, 128, 114, 104, 72 |
| 40 | N,N-disilyl-2-picolylamine | 168.34 | 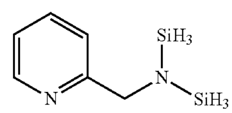 | 168, 167, 153, 135, 120, 108, 93 |
| 41 | N,N-disilyl-2-(2-pyridyl)ethylamine | 182.37 | 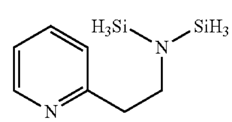 | 182, 181, 151, 122, 106, 90 |
| 42 | N,N-disilyl-1-(4-methylphenyl)ethylamine | 195.41 | 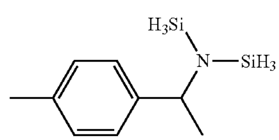 | 195, 180, 164, 148, 119, 105, 91 |

Example 3

Figure 2:
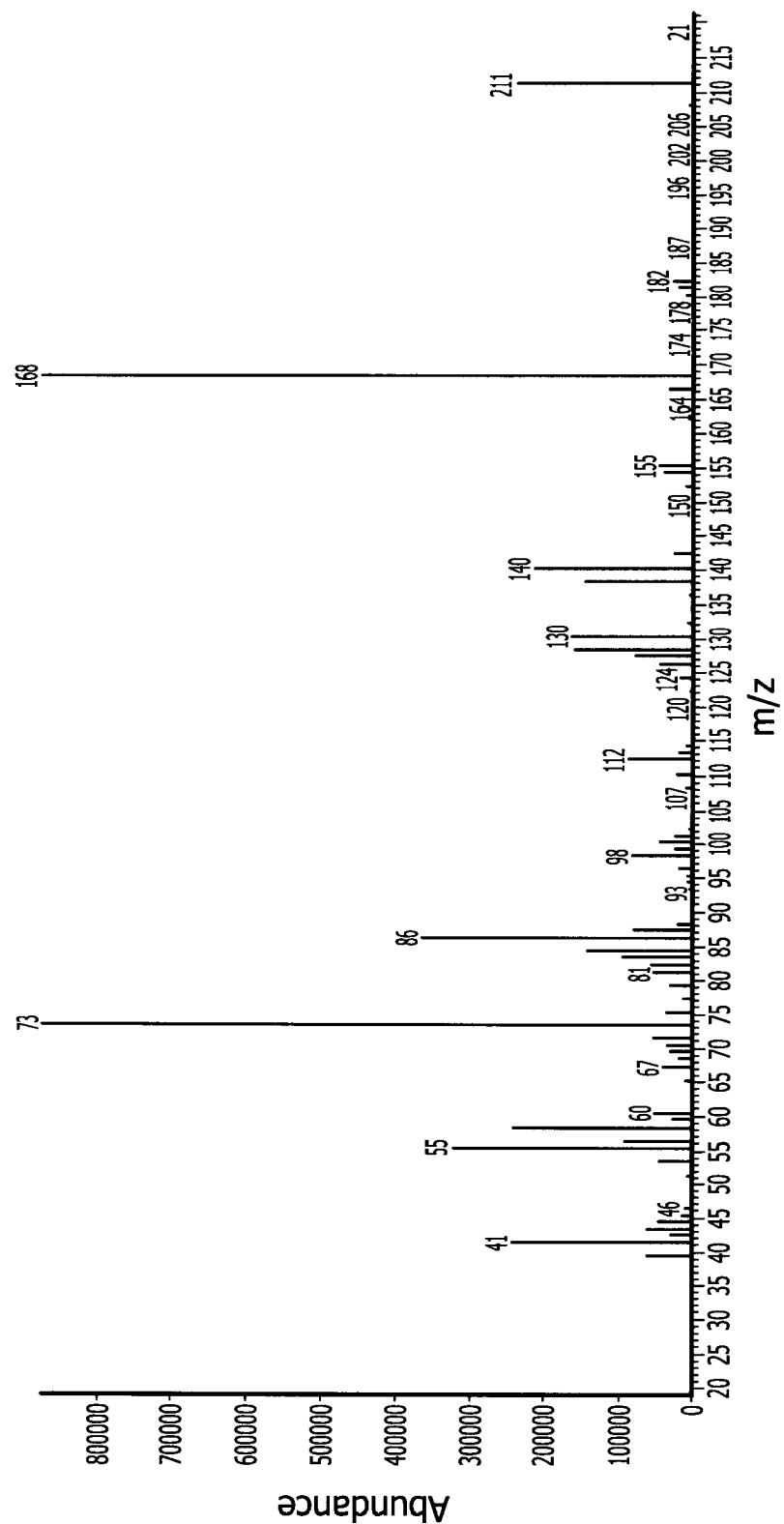
FIG. 2 provides the mass spectroscopy (MS) spectrum of dicyclohexylaminosilane having Formula A described herein and described in Table III no. 7.
Figure 3:
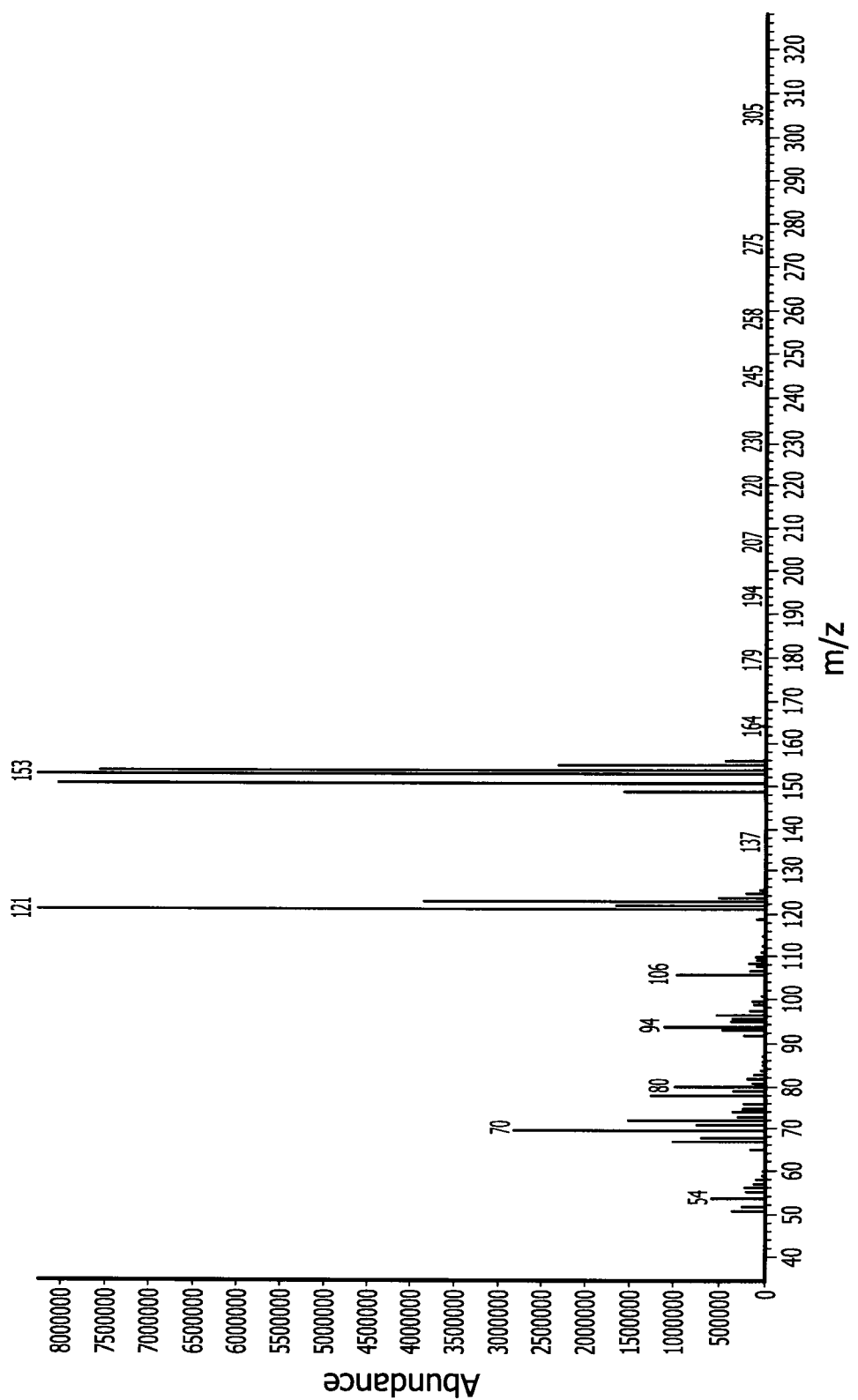
FIG. 3 provides the mass spectroscopy (MS) spectrum of N-2-pyridyldisilazane having Formula B described herein and in Example 2.
Figure 4:
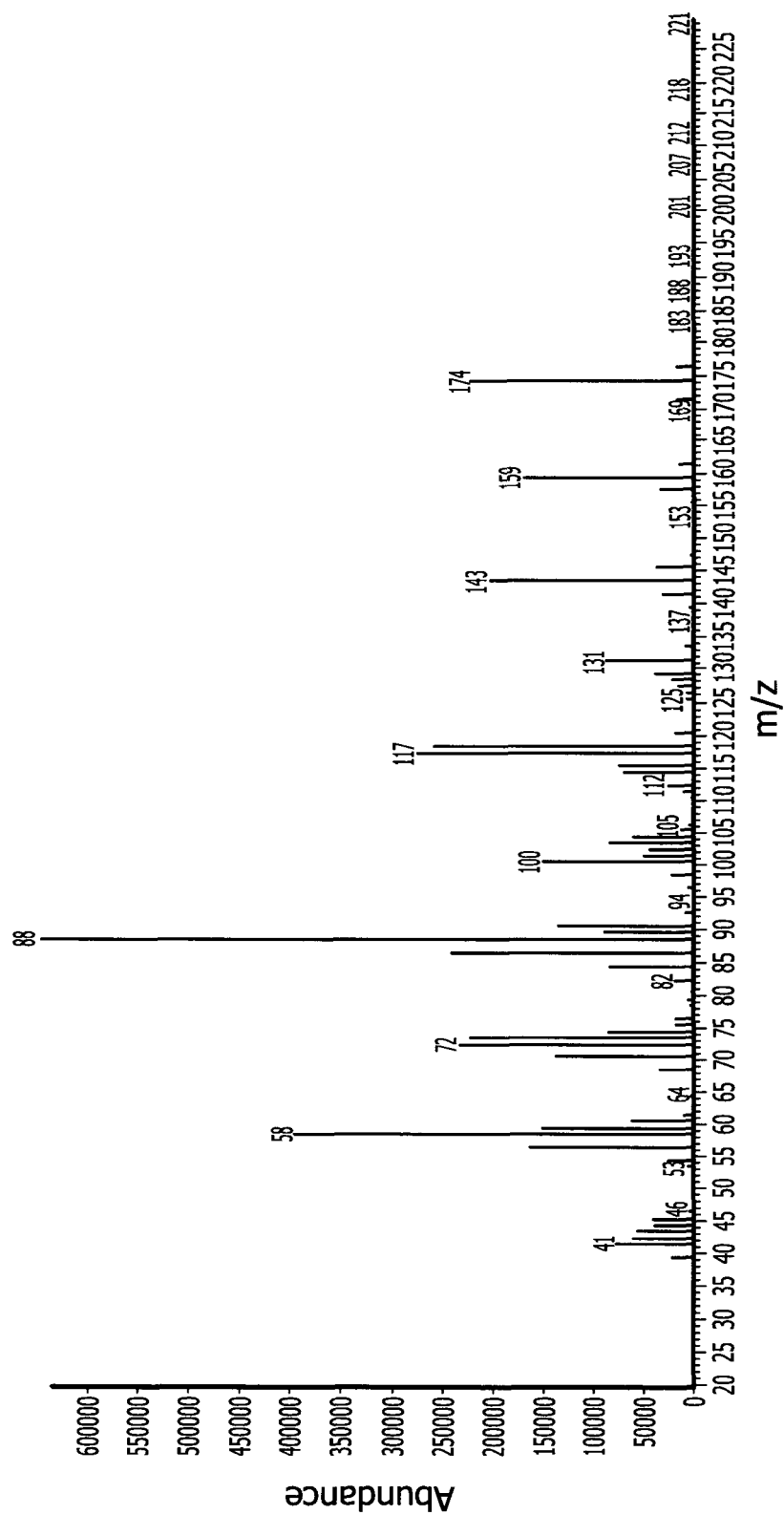
FIG. 4 provides the mass spectroscopy (MS) spectrum of N,N'-disilyl-trans-2,5-dimethylpiperizine having Formula C described herein and in Example 3.
Figure 5:
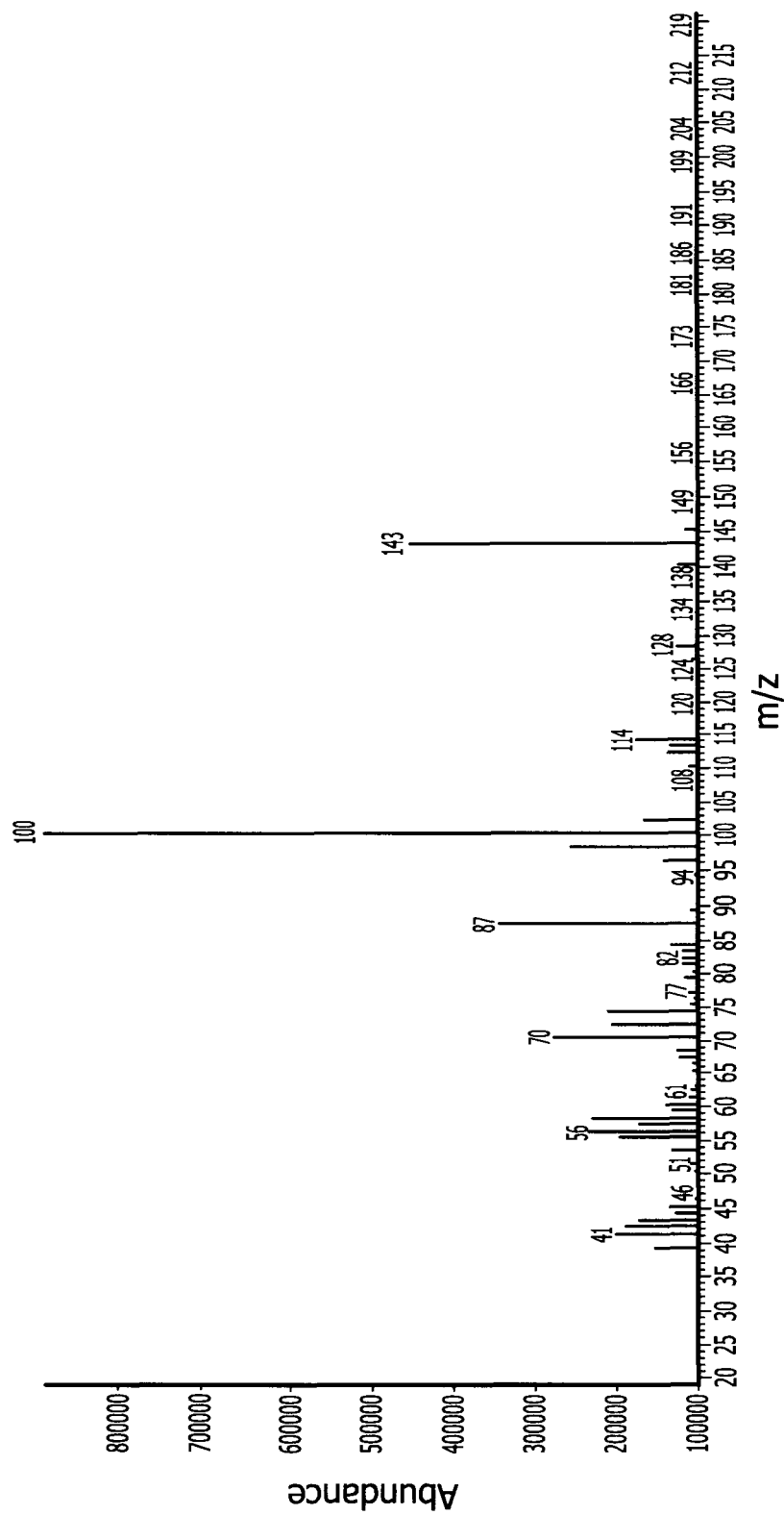
FIG. 5 provides the mass spectroscopy (MS) spectrum of N-methylcyclohexylaminosilane having Formula A described herein and described in Table III no. 5.
Figure 6:
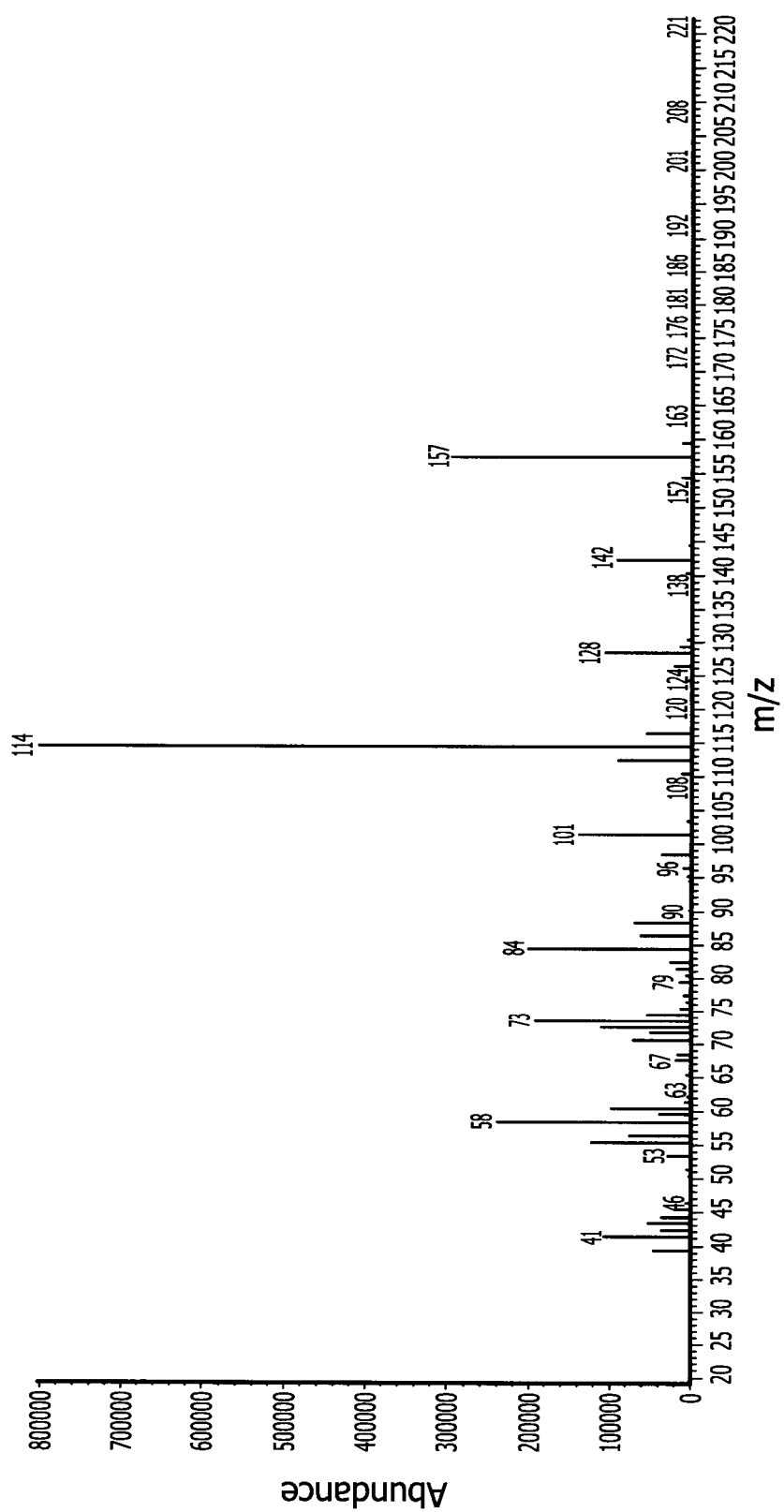
FIG. 6 provides the mass spectroscopy (MS) spectrum of N-ethylcyclohexylaminosilane having Formula A described herein and described in Table IIII no. 6.

Synthesis of N,N'-disilyl-trans-2,5-dimethylpiperizine and Other Organoaminosilane Precursors Having Formula C In a 500 ml Schlenk flask 57 (0.5 mol) trans-2,5-dimethylpiperizine and 196.5 g (1.5 mol) di-isopropylaminosilane were stirred at ambient temperature under nitrogen atmosphere for 12 hours. The relatively lower boiling point byproduct di-isopropylamine was removed with vacuum at a pressure of 20 mmHg and room temperature (25° C.). The reaction mixture was then stirred for another 12 hours. The product N,N'-disilyl-trans-2,5-dimethylpiperizine (78 g, 90% yield) was obtained by vacuum distillation with boiling point of 54° C. at 10 mm Hg. The end-product was characterized by mass spectroscopy (MS) which is provided in FIG. 2 and shows, among other things, peaks at 174 (M+), 159 (M-CH$_3$), 143 (M-SiH$_3$), 131, 117, 100, 83, 72, and 58. The molecular weight of the N,N'-disilyl-trans-2,5-dimethylpiperizine was 174.39.

Additional organoaminosilane precursors were made in accordance with the reaction scheme described herein in Equation (6) using di-iso-propylaminosilane and one or more of the following amines provided in Table II (Formula B or C) to provide a reaction mixture and the reaction mixture is stirred at ambient temperature under a nitrogen atmosphere for 12 hours. The choice of amine selected influenced the desired resulting end-product precursor. For example, N,N'-di(2-yrimidino)trisilazane was made from a reaction mixture comprising di-iso-propylaminosilane and 2-aminopyrimidine. The relatively lower boiling point byproduct di-isopropylamine was removed with vacuum at a pressure of 20 mmHg and room temperature (25° C.). The reaction mixture was then stirred for another 12 hours. The desired organoaminosilane end-product having Formula C was obtained by vacuum distillation. The end-product was characterized by mass spectroscopy (MS) and the peaks and molecular weight for each end-product is provided in Table V.

TABLE V

Organoaminosilanes Having Formula C

| No. | Precursor Name | MW | Structure | MS Peaks |
|---|---|---|---|---|
| 1 | N,N'-dicyclopropyltrisilazane | 202.08 | 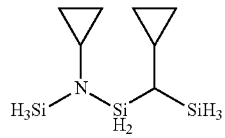 | 201, 187, 173, 159, 146, 132, 116, 104, 86 |
| 2 | N,N'-diisopropyltrisilazane | 206.11 | 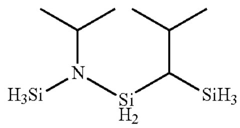 | 206, 191, 175, 161, 147, 117, 106, 86 |
| 3 | N,N,N'N'-tetrasilyl-1,4-phenylenediamine | 228.54 | 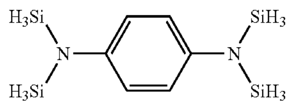 | 228, 196, 153, 138, 120, 98 |
| 4 | N,N'-dicyclopentyltrisilazane | 259.58 | 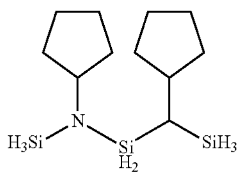 | 258, 257, 227, 201, 187, 159, 143, 133, 114, 86 |
| 5 | 1,4-disilyl-2,3,5,6-tetramethylpiperazine | 202.44 | 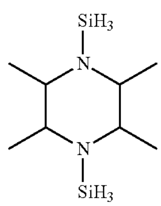 | 202, 187, 171, 145, 131, 114, 102, 74 |
| 6 | 1,4-disilyl-2,6-dimethylpiperazine | 174.39 | 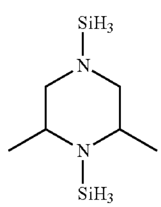 | 173, 143, 128, 114, 100, 86 |
| 7 | N,N'-di(cyclopropanemethyl)trisilazane | 230.53 | 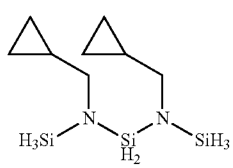 | 230, 229, 199, 187, 173, 159, 145, 129, 119, 102 |
| 8 | N,N'-dicyclobutyltrisilazane | 230.11 | 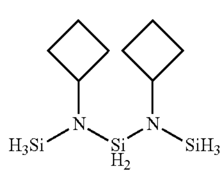 | 230, 229, 199, 187, 173, 159, 145, 129, 119, 102 |
| 9 | N,N'-dicycloheptyltrisilazane | 314.20 | 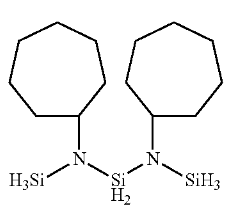 | 314, 283, 257, 229, 217, 159, 133 |

TABLE V-continued

Organoaminosilanes Having Formula C

| No. | Precursor Name | MW | Structure | MS Peaks |
|---|---|---|---|---|
| 10 | N,N'-di(2-pyrimidino)trisilazane | 278.49 | (structure) | 277, 247, 220, 193, 165, 152, 122, 101 |
| 11 | 1,4-disilyl-2,5-dimethylpiperazine | 174.39 | (structure) | 174, 159, 143, 131, 117, 100, 86 |

Example 4

Computer Simulation of Relative Chemical Stability of Formula a Precursors

To understand the thermal stability of the precursor candidates for a deposition process, quantum mechanical calculations were performed on the following Formula A precursors: N-silyldecahydroquinoline, N-methylcyclohexylaminosilane, N-ethylcyclohexylaminosilane, N-isopropylcyclohexylaminosilane, and dicyclohexylaminosilane. The quantum mechanical calculations were obtained using the density functional theory (DFT) to evaluate the kinetics and thermodynamics behavior of the following scrambling reaction:

$$2SiH_3L \rightarrow SiH_4 + SiH_2L_2$$

(where L=decahydroquinoline, N-methylcyclohexylamino, N-ethylcyclohexylamino, N-iso-propylcyclohexylamino and dicyclohexylamino groups).

This particular reaction was chosen for the simulation because of experimental evidence of the formation of silane ($SiH_4$) which is a potential safety hazard due to pressure buildup in the cylinder headspace. This reaction is the first and generally accepted as rate limiting in the series of analogous steps generating $SiX_4$ and $SiH_4$ as final products. The calculations were performed in the all electron approximation using the BLYP density functional consisting of the B88 exchange functional (Becke, Phys. Rev. A 38, 3098 1988) and the LYP correlation functional (Lee Yang Parr, Phys. Rev. B 37, 785 1988) in conjunction with a double numerical polarized basis set and 4.0 °A global cutoff as implemented in the $Dmol^3$ module of Materials Studio® 5.5 by Accelrys (B. Delley, J. Chem. Phys. 92, 508 1990; B. Delley, J. Chem. Phys. 113, 7756 2000).

The results of the calculations are provided in Table VI. It can be seen from the Table VI that all reactions are thermally favored or close to thermal neutrality (indicated by the negative or close to zero energy of reaction, $E_{rxn}$). Table VI also shows that increasing the bulkiness on the carbon atoms attached to the nitrogen atom increases the activation energy ($E_a$) for the scrambling reaction which indicates increasing thermal stability with respect to this thermal decomposition mechanism via slowing down the kinetics. Increasing activation energy results in a fewer portion of the molecules with enough energy to overcome the energy barrier between the reactant and the product (the formation of which would otherwise be favored thermodynamically). The results is a slowdown of the chemical reaction at a given temperature, or, alternatively, a raise in the temperature needed to reach a certain rate of decomposition by this mechanism.

TABLE VI

Comparison of Relative Chemical Stability
(Energies expressed in kcal/mol)

| Precursor: | $E_a$ | $E_{rxn}$ |
|---|---|---|
| N-silyldecahydroquinoline (Table I no. 16) | 48.3 | −0.1 |
| N-methylcyclohexylaminosilane (Table I no. 5) | 38.6 | −3.6 |
| N-ethylcyclohexylaminosilane (Table I no. 6) | 41.4 | −3.8 |
| N-isopropylcyclohexylaminosilane (Table I no. 17) | 51.2 | −2.8 |
| Dicyclohexylaminosilane (Table I no. 7) | 55.5 | +1.0 |

Example 5

Atomic Layer Deposition of Silicon Oxide Films

Atomic layers depositions of silicon oxide films were conducted using the following Formula A precursors: N-methylcyclohexylaminosilane, N-ethylcyclohexylaminosilane, and N-isopropylcyclohexylaminosilane. The depositions were performed on a laboratory scale ALD processing tool. All gases (e.g., purge and reactant gas or precursor and oxygen source) were preheated to 100° C. prior to entering the deposition zone. Gases and precursor flow rates were controlled with ALD diaphragm valves having high speed actuation. The substrates used in the deposition were 12 inch length silicon strips having thermocouples attached on a sample holder to confirm the substrate temperature. Depositions were performed using a baseline of 400 cycles with ozone as the oxygen source gas and the process parameters of the depositions are provided in Table VII.

TABLE VII

Process for Generating Basic ALD Oxide Films with O₃

| Step 1 | 6 seconds (sec) | Nitrogen Purge of Reactor | Flow 1.5 slpm N₂ | Purges out unreacted chemical from reactor |
|---|---|---|---|---|
| Step 2 | 6 sec | Chamber evacuation | <100 mT | Preps the reactor for the precursor dose |
| Step 3 | 2 sec | Close throttle valve | | Increases precursor resonance time |
| Step 4 | variable | Dose Silicon Precursor | | Reactor pressure typically <1 T during dose |
| Step 5 | 6 sec | Nitrogen Purge of Reactor | Flow 1.5 slpm N₂ | Purges out unreacted chemical from reactor |
| Step 6 | 6 sec | Chamber evacuation | <100 mT | Preps the reactor for the precursor dose |
| Step 7 | 2 sec | Close throttle valve | | Increases precursor resonance time |
| Step 8 | 4 sec | Dose Ozone | | O₃ at 15-20% post generator, P = <8 T |

The resultant SiO₂ films were characterized for deposition rate and refractive index. Thickness and refractive indices of the films was measured using a FilmTek 2000SE ellipsometer by fitting the reflection data from the film to a pre-set physical model (e.g., the Lorentz Oscillator model). For refractive index, a value of around 1.44 to 1.47 would reflect a typical CVD silicon oxide film. All of the precursors tested deposited films having a refractive index of ranging from about 1.4 to about 1.5.

Figure 7:
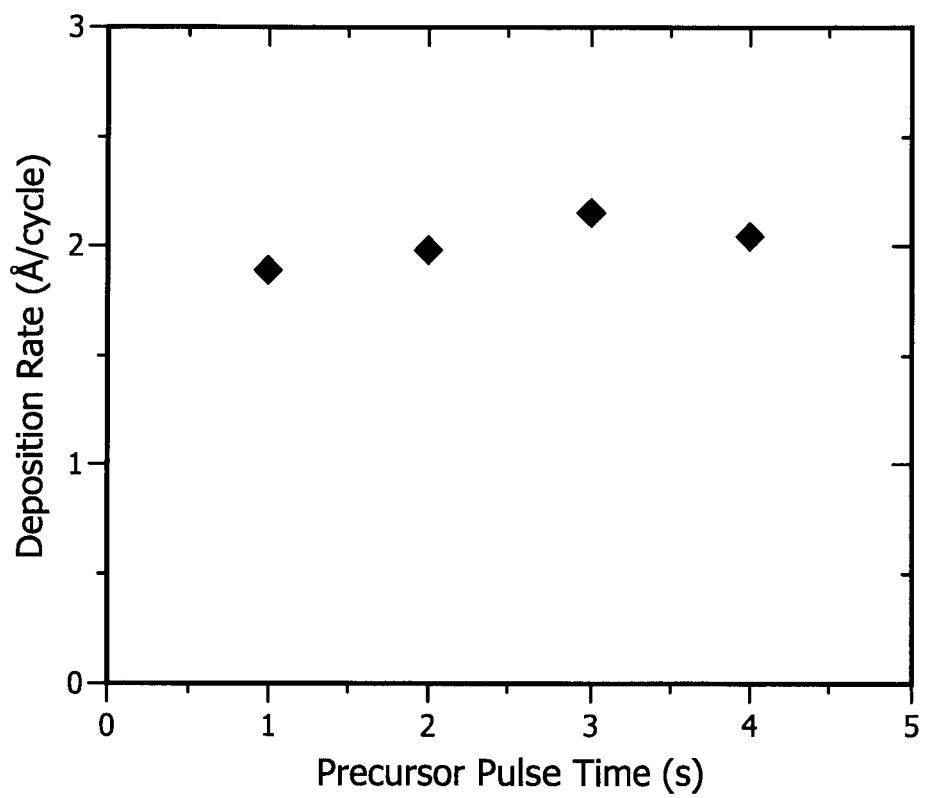
FIG. 7 provides the deposition rate of silicon oxide films deposited using the N-methylcyclohexylaminosilane precursor as function of precursor pulse time as described in Example 5.

Silicon oxide films were deposited via ALD at a 150° C. substrate temperature using N-methylcyclohexylaminosilane and ozone. The N-methylcyclohexylaminosilane precursor was delivered at 17 Torr with pulse time ranging from 1 second to 5 seconds while ozone flow is fixed to 4 seconds at 5000 sccm. FIG. 7 shows that the deposition rate for the N-methylcyclohexylaminosilane films was independent to precursor pulse time, exhibiting self limiting behavior, at 2 Å/cycle. Refractive index of the films was between 1.45 and 1.47, which is typical for silicon oxide films.

Silicon oxide films were deposited via ALD at deposited at 75° C., 100° C. and 150° C. temperature using N-methylcyclohexylaminosilane and ozone. The N-methylcyclohexylaminosilane precursor was delivered at 17 Torr for 2 seconds while ozone flow was fixed to 4 seconds at 5000 sccm. Table VIII provides deposition rate as a function of substrate temperature.

Silicon oxycarbide films were deposited via ALD at various temperatures ranging from 45° C. to 150° C. using N-ethylcyclohexylaminosilane and ozone. The N-ethylcyclohexylaminosilane precursor was delivered at 9 Torr for 2 seconds while ozone flow was fixed to 4 seconds at 5000 sccm. Table VIII provides the deposition rate as function of substrate temperature. Refractive index for the deposited films is also provided in Table VIII. Refractive index of the N-ethylcyclohexylaminosilane deposited films decreased from 1.60 to 1.45 with increasing temperature. A higher refractive index indicates more carbon dopant in the silicon oxide films.

Silicon oxycarbide films were deposited via ALD at various temperatures ranging from 45° to 300° C. using N-isopropylcyclohexylaminosilane and ozone. The N-isopropylcyclohexylaminosilane precursor was delivered at 3 Torr for 4 seconds while ozone flow was fixed to 2 seconds at 5000 sccm. Table VIII provides the deposition rate as function of substrate temperature. Refractive index for the deposited films is also provided in Table VIII. Refractive index of the N-ethylcyclohexylaminosilane deposited films decreased from 1.77 to 1.50 with increasing temperature. A comparison of the deposition rates versus temperature for the films deposited using N-methylcyclohexylaminosilane, N-ethylcyclohexylaminosilane, N-isopropylcyclohexylaminosilane is provided in Table VIII. Table VIII shows that larger R substituent groups such as isopropyl provides steric hindrance during the deposition process which resulting in a lower deposition rate as well as more carbon incorporation as evidenced by the higher refractive index than a smaller R substituent such as methyl. However, it is highly possible that the carbon content can be reduced via tuning ALD conditions such as using other oxidant than ozone, allowing N-ethylcyclohexylaminosilane or N-isopropylcyclohexylaminosilane to be employed to deposit high purity silicon oxide.

TABLE VIII

ALD Deposition Results

| Film No. | Precursor | Wafer Temp | Dep. Rate (Å/cycle) | Refractive Index |
|---|---|---|---|---|
| 1 | N-methylcyclohexylaminosilane | 75 | 1.2 | 1.48 |
| 2 | N-methylcyclohexylaminosilane | 100 | 1.7 | 1.47 |
| 3 | N-methylcyclohexylaminosilane | 150 | 2.0 | 1.45 |
| 4 | N-ethylcyclohexylaminosilane | 45 | 0.4 | 1.60 |
| 5 | N-ethylcyclohexylaminosilane | 75 | 1.6 | 1.50 |
| 6 | N-ethylcyclohexylaminosilane | 150 | 1.5 | 1.77 |
| 7 | N-ethylcyclohexylaminosilane | 300 | 2.0 | 1.45 |
| 8 | N-isopropylcyclohexylaminosilane | 45 | 0.3 | 1.77 |
| 9 | N-isopropylcyclohexylaminosilane | 75 | 0.9 | 1.50 |

The invention claimed is:

1. An organoaminosilane represented by one of the following Formulas A, B, or C:

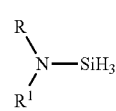

A

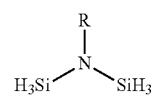

B

-continued

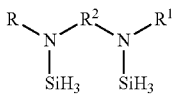

wherein R is independently selected from a $C_3$ to $C_{10}$ branched, alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_3$ to $C_{10}$ alkenyl group; a $C_1$ to $C_{10}$ alkoxy group; a $C_1$ to $C_{10}$ alkylamino group; and in Formula C, R can also be a silyl group with or without substituents;

wherein $R^1$ is independently selected from a $C_3$ to $C_{10}$ linear, branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_3$ to $C_{10}$ alkenyl group; a $C_1$ to $C_{10}$ alkoxy group; a $C_1$ to $C_{10}$ alkylamino group; or a silyl group with substituents; and wherein $R^2$ represents a single bond; a saturated or unsaturated, linear or branched, substituted or unsubstituted hydrocarbon chain wherein a number of carbon atoms ranges ranging from 1 to 10; a saturated or unsaturated carbocyclic or heterocyclic ring; $SiR_2$; or $SiH_2$, and wherein R and $R^1$ in Formula A are also combinable to form a cyclic group and wherein anyone or more of R, $R^1$ and $R^2$ in Formula C are also combinable to form a cyclic group provided that the organoaminosilane is one selected from the group consisting of the following:
  (a) the organoaminosilane comprises 1-silyl-7-azaindole;
  (b) the organoaminosilane comprises N-silyl-2,5-dimethylpyrrole;
  (c) the organoaminosilane having Formula B wherein R is a substituted $C_5$-$C_{10}$ aromatic group comprising one or more of the following substituents: an alkyl group, an alkenyl group, and an alkoxy group;
  (d) the organoaminosilane having Formula B wherein R is a substituted $C_2$ to $C_{10}$ alkyl group wherein the alkyl group is substituted with one or more of the following: a hetero atom, an aromatic group, an alkylamino group, or an alkoxy group.

2. A composition for the deposition of a silicon containing film comprising:
  an organoaminosilane having Formula A, B, and C or mixtures thereof:

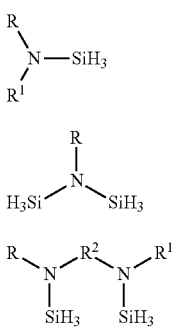

wherein R is independently selected from a $C_1$ to $C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_3$ to $C_{10}$ alkenyl group; a $C_1$ to $C_{10}$ alkoxy group; a $C_1$ to $C_{10}$ alkylamino group; and in Formula C, R can also be a silyl group with or without substituents; $R^1$ is independently selected from a $C_3$-$C_{10}$ linear or branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_3$ to $C_{10}$ alkenyl group; a $C_1$ to $C_{10}$ alkoxy group; a $C_1$ to $C_{10}$ alkylamino group; or a silyl group with substituents; and $R^2$ represents a single bond; a saturated or unsaturated, linear or branched, substituted or unsubstituted, hydrocarbon chain wherein the number of carbon atoms ranges from 1 to 10; a saturated or unsaturated, carbocyclic or heterocyclic ring; $SiR_2$; or $SiH_2$, and wherein R and $R^1$ in Formula A are also combinable to form a cyclic group; and a solvent selected from the group consisting of an ether, a tertiary amine, a nitrile, a tertiary amino ether, or mixtures thereof.

3. The composition of claim 2 wherein the organoaminosilane and the solvent each has a boiling point and wherein the difference between the boiling point of the organoaminosilane and the boiling point of the solvent is 40° C. or less.

4. The composition of claim 2 wherein the organoaminosilane and the solvent each has a boiling point and wherein the difference between the boiling point of the organoaminosilane and the boiling point of the solvent is 20° C. or less.

5. An organoaminosilane of following Formula A:

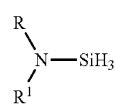

wherein R is independently selected from a $C_1$ to $C_{10}$ linear or branched, alkyl group;

a $C_3$ to $C_{10}$ cyclic alkyl group; a $C_5$ to $C_{10}$ aromatic group; a $C_3$ to $C_{10}$ saturated or unsaturated heterocyclic group; a linear or a branched $C_3$ to $C_{10}$ alkenyl group; a $C_1$ to $C_{10}$ alkoxy group; or a $C_1$ to $C_{10}$ alkylamino group;

wherein $R^1$ is independently selected from a $C_3$ to $C_{10}$ linear, branched alkyl group; a $C_3$ to $C_{10}$ cyclic alkyl group; a $C_5$ to $C_{10}$ aromatic group; a $C_3$ to $C_{10}$ saturated or unsaturated heterocyclic group; a hydrogen atom; a linear or a branched $C_3$ to $C_{10}$ alkenyl group; a $C_1$ to $C_{10}$ alkoxy group; or a $C_1$ to $C_{10}$ alkylamino group; and provided that R and $R^1$ in Formula A are one selected from the group consisting of the following:
  (a) the organoaminosilane comprises 1-silyl-7-azaindole;
  (b) R and $R^1$ are combined to form a 5 or 6 member heterocyclic substituted or unsubstituted, aliphatic ring and wherein the organoaminosilane comprises N-silyldecahydroquinoline;
  (c) R and $R^1$ are the same substituents provided that both R and $R^1$ are not one of the following groups: ethyl, isopropyl, tert-butyl, isobutyl, sec-butyl, n-butyl, t-pentyl, and sec-pentyl groups; or
  (d) R and $R^1$ are different substituents.

6. The organoaminosilane of claim 5 wherein R and $R^1$ are different substitutents and wherein the organoaminosilane is one selected from the group consisting of: N-propyl-isopropylaminosilane, N-methylcyclohexylaminosilane, N-ethyl-cyclohexylaminosilane-, allylphenylaminosilane, N-isopropylcyclohexylaminosilane, allylcyclopentylaminosilane, phenylcyclohexylaminosilane, and 2-(N-silylmethylamino) pyridine.

7. An organoaminosilane of following Formula B:

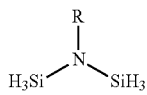

wherein R is selected from a $C_6$ to $C_{10}$ substituted aromatic group which is substituted with at least one substituent selected from the group consisting of an alkyl group, an alkenyl group, an amino group, and an alkoxy group or an unsubstituted aromatic group provided that R is not phenyl; a linear or a branched, substituted or unsubstituted $C_3$ to $C_{10}$ alkenyl group; a $C_1$ to $C_{10}$ alkoxyalkyl group; a $C_1$ to $C_{10}$ alkylamino or dialkylamino group; or a $C_4$ to $C_{10}$ linear or branched, substituted or unsubstituted alkyl group provided that R is not an unsubstituted tert-butyl, t-pentyl, or cyclohexyl group.

8. The organoaminosilane of claim 7 which is one selected from the group consisting of: N-(4-methoxyphenyl)disilazane, N-(3-methoxyphenyl)disilazane, N-(2-methoxyphenyl)disilazane, N-(4-chlorophenyl)disilazane, N-(2-chlorophenyl)disilazane, N-(2-ethylphenyl)disilazane, N-(2,6-diethylphenyl)disilazane, N-(2-propylphenyl)disilazane, N-(4-t-butylphenyl)disilazane, N-(4-iso-propylphenyl)disilazane, N-(2-iso-propylphenyl)disilazane, N-(3-ethylphenyl) disilazane, N-(4-sec-butylphenyl)disilazane, N-(4-vinylphenyl)disilazane, N-(3-methylphenyl)disilazane, N-(4-methylphenyl)disilazane, N-(2,4,6-trimethylphenyl)disilazane, and N-(2, 6-di-isopropylphenyl)disilazane.

9. An organoaminosilane selected from the group consisting of:
1-N-(2-pyridyl)disilazane, N,N-disilyl-2-aminopyrimidine, N-(4-methyl-2-pyridyl)disilazane, N-(6-methyl-2-pyridyl)disilazane, N-(3-methyl-2-pyridyl)disilazane, N-(5-methyl-2-pyridyl)disilazane, and N-[2-(4-methylpyrimidino)amino]disilazane.

10. An organoaminosilane selected from the group consisting of, N-(2-dimethylamino-1-methylethyl)disilazane, N-(2-dimethylaminoethyl)disilazane, N-(1-cyclohexylethyl)disilazane, N,N-disilylcumylamine, N-[3,3-dimethylbutyl-2]ldisilazane, N,N-disilyl-2-picolylamine, N,N-disilyl-2-(2-pyridyl)ethylamine, and N,N-disilyl-1-(4-methylphenyl)ethylamine.

* * * * *